(12) United States Patent
Tauch et al.

(10) Patent No.: US 8,334,126 B2
(45) Date of Patent: Dec. 18, 2012

(54) CORYNEFORM HOST-VECTOR SYSTEMS COMPRISING A CHROMOSOMAL ALR GENE WHICH IS ATTENUATED OR ELIMINATED AND METHODS OF USING

(75) Inventors: Andreas Tauch, Bielefeld (DE); Michael Binder, Hasselroth (DE); Walter Pfefferle, Langgöns (DE); Georg Thierbach, Bielefeld (DE); Jörn Kalinowski, Bielefeld (DE); Alfred Pühler, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/240,147

(22) Filed: Sep. 22, 2011

(65) Prior Publication Data

US 2012/0064582 A1    Mar. 15, 2012

Related U.S. Application Data

(60) Division of application No. 10/304,743, filed on Nov. 27, 2002, now Pat. No. 8,048,665, which is a continuation-in-part of application No. 09/909,849, filed on Jul. 23, 2001, now abandoned.

(60) Provisional application No. 60/220,188, filed on Jul. 24, 2000, provisional application No. 60/292,510, filed on May 23, 2001.

(51) Int. Cl.
C12N 9/00 (2006.01)
C12N 9/90 (2006.01)
C12N 1/20 (2006.01)
C12N 15/00 (2006.01)

(52) U.S. Cl. ............... 435/233; 435/183; 435/252.3; 435/320.1; 536/23.2

(58) Field of Classification Search ................ None
See application file for complete search history.

(56) References Cited

U.S. PATENT DOCUMENTS 5,728,555 A * 3/1998 Fotheringham et al. ...... 435/106

OTHER PUBLICATIONS

Sonnen et al. Gene. Oct. 30, 1991;107(1):69-74 (Abstract).*

* cited by examiner

*Primary Examiner* — Christian Fronda
(74) *Attorney, Agent, or Firm* — Smith, Gambrell & Russell, LLP

(57) ABSTRACT

The invention relates to an isolated polynucleotide having a polynucleotide sequence which codes for the alr gene, and a host-vector system having a coryneform host bacterium in which the alr gene is present in attenuated form and a vector which carries at least the alr gene according to SEQ ID No 1, and the use of polynucleotides which comprise the sequences according to the invention as hybridization probes.

13 Claims, 8 Drawing Sheets

CORYNEFORM HOST-VECTOR SYSTEMS COMPRISING A CHROMOSOMAL ALR GENE WHICH IS ATTENUATED OR ELIMINATED AND METHODS OF USING

CROSS-REFERENCE TO RELATED APPLICATIONS

This application is a divisional of U.S. patent application Ser. No. 10/304,743, filed 27 Nov. 2002, issued as U.S. Pat. No. 8,048,665, which is a continuation-in-part of U.S. patent application Ser. No. 09/909,849, filed 23 Jul. 2001 now abandoned, both of which are hereby incorporated by reference in their entirety. This application claims priority to U.S. Patent Application Ser. No. 60/220,188, filed 24 Jul. 2000 and 60/292,510, filed 23 May 2001. Both provisional applications are hereby incorporated by reference in their entirety.

BACKGROUND OF THE INVENTION

The invention provides nucleotide sequences of coryneform bacteria which code for the alr gene, a host-vector system for coryneform bacteria using the alr gene, processes for the preparation of chemical compounds using the host-vector system and processes for the preparation of D-amino acids, in particular D-alanine or D-valine, using coryneform bacteria or Enterobacteriaceae in which the alr gene of coryneform bacteria is present in enhanced form. All references cited herein are expressly incorporated by reference. Incorporation by reference is also designated by the term "I.B.R." following any citation.

Chemical compounds, which means, in particular, L-amino acids, vitamins, nucleosides and nucleotides and D-amino acids, are used in human medicine, in the pharmaceuticals industry, in cosmetics, in the foodstuffs industry and in animal nutrition.

Numerous of these compounds are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce the particular compounds are obtained in this manner.

Methods of the recombinant DNA technique have also been employed for some years for improving the strain of *Corynebacterium* strains, by amplifying individual biosynthesis genes and investigating the effect on production.

Naturally occurring plasmids and plasmid vectors prepared from these are an important prerequisite for improving the production properties of coryneform bacteria. The construction of plasmid vectors for this group of industrially important bacteria is substantially based on cryptic plasmids which are equipped with suitable antibiotic resistance markers capable of functioning in *Corynebacteria* or *Brevibacteria* (U.S. Pat. No. 5,158,891 I.B.R. and U.S. Pat. No. 4,500, 640 I.B.R.). These plasmid vectors can be employed for cloning and enhancing genes which participate in the production of chemical compounds, such as, for example, L-amino acids, vitamins or nucleosides and nucleotides. Production of the desired substances can be influenced in a positive manner by expression of the particular genes. Thus e.g. cloning of a DNA fragment which codes a protein for a lysine exporter led to an improvement in the fermentative production of L-lysine with *Corynebacterium glutamicum* strain MH20-22B (DE-A 19548222 I.B.R.).

In contrast to the known bacterium of equal industrial importance *Escherichia coli*, only a limited number of natural plasmids and suitable selection markers for the development of cloning and expression vectors are known for *Corynebacteria* and *Brevibacteria*, in particular *Corynebacterium glutamicum*. Selection systems have hitherto been available only in the form of two antibiotic resistance markers which have been identified on the streptomycin/spectinomycin resistance plasmid pCG4 from *Corynebacterium glutamicum* ATCC31830 (U.S. Pat. No. 4,489,160 I.B.R.) and on the tetracycline resistance plasmid pAG1 from *Corynebacterium melassecola* 22243 (U.S. Pat. No. 5,158,891 I.B.R.). Plasmid pCG4 furthermore carries the sulI gene, which imparts sulfamethoxazole resistance and the sequence of which was determined by Nesvera et al. (FEMS Microbiology Letters 169, 391-395 (1998) I.B.R.).

For rapid investigation and improvement of strains which produce the compounds mentioned, it is important to have plasmid vectors which are compatible with one another and have a sufficiently high stability, such as e.g. the plasmid pGA1 from *Corynebacterium glutamicum* LP-6 (U.S. Pat. No. 5,175,108 I.B.R.). The plasmid vectors conventionally employed are composed of components which originate from the species *Corynebacterium glutamicum* and another species of bacteria, typically *Escherichia coli*. Foreign DNA is introduced into the species *Corynebacterium glutamicum* by this procedure. Stable plasmid vectors which are capable of functioning and contain only species-characteristic DNA with an antibiotic-free selection possibility and therefore meet the criteria of self-cloning are not known to experts.

Processes for the preparation of D-amino acids with *Corynebacterium glutamicum* by fermentative or biocatalytic methods are not known to experts.

BRIEF SUMMARY OF THE INVENTION

The invention provides new host-vector systems for coryneform bacteria.

The inventors furthermore had the object of providing new measures for improved preparation of D-amino acids.

SUMMARY OF THE INVENTION

The invention provides an isolated polynucleotide from coryneform bacteria, comprising a polynucleotide sequence which codes for the alr gene, chosen from the group consisting of a) polynucleotide which is identical to the extent of at least 70% to a polynucleotide which codes for a polypeptide which comprises the amino acid sequence of SEQ ID No. 9, b) polynucleotide which codes for a polypeptide which comprises an amino acid sequence which is identical to the extent of at least 70% to the amino acid sequence of SEQ ID No. 9, c) polynucleotide which is complementary to the polynucleotides of a) or b), and d) polynucleotide comprising at least 15 successive nucleotides of the polynucleotide sequence of a), b) or c)

the polypeptide preferably having the activity of alanine racemase (EC No. 5.1.1.1).

The invention provides a polynucleotide, this preferably being a DNA which is capable of replication, comprising:
(i) the nucleotide sequence shown in SEQ ID No. 8, or
(ii) at least one sequence which corresponds to sequence (i) within the range of the degeneration of the genetic code, or
(iii) at least one sequence which hybridizes with the sequence complementary to sequence (i) or (ii), and optionally
(iv) sense mutations of neutral function in (i).

The invention also provides
a polynucleotide, comprising the nucleotide sequence as shown in SEQ ID No. 8,
a polynucleotide which codes for a polypeptide which comprises the amino acid sequence as shown in SEQ ID No. 9,
a vector containing the polynucleotide according to SEQ ID No. 8 or parts thereof, in particular a shuttle vector or plasmid vector,
bacteria which contain the above-mentioned vector,
coryneform bacteria, in which the chromosomal alr gene is present in attenuated, preferably eliminated, form,
and bacteria, in particular coryneform bacteria and Enterobacteriaceae, in which the alr gene of coryneform bacteria is present in enhanced form, optionally in combination with the attenuation or elimination of the chromosomal alr gene.

The invention also provides polynucleotides which substantially comprise a polynucleotide sequence, which are obtainable by screening by means of hybridization of a corresponding gene library, which comprises the complete gene with the polynucleotide sequence corresponding to SEQ ID No. 8, with a probe which comprises the sequence of the polynucleotide mentioned, according to SEQ ID No. 8 or a fragment thereof, and isolation of the DNA sequence mentioned.

DETAILED DESCRIPTION OF THE INVENTION

Figure 1:
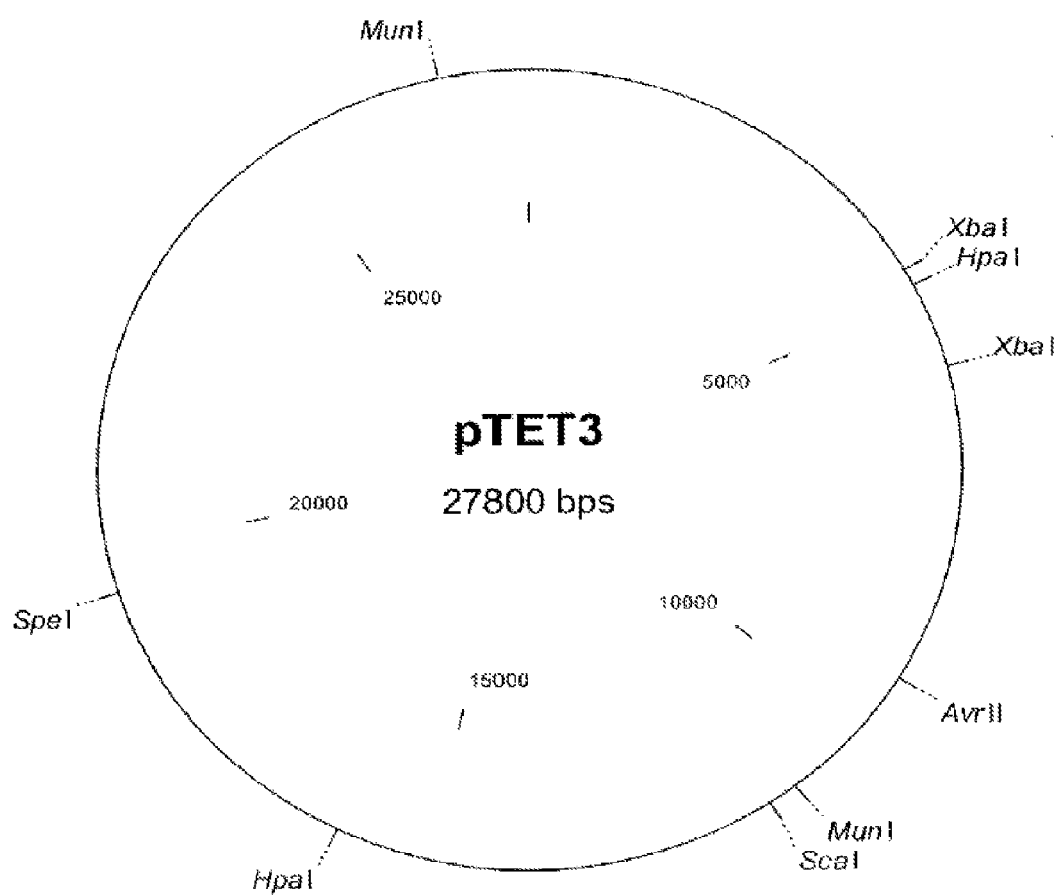
FIG. 1 is a restriction map of the plasmid pTET3.

Polynucleotides which comprise the sequences according to the invention are suitable as hybridization probes for RNA, cDNA and DNA, in order to isolate, in the full length, polynucleotides or genes which code for alanine racemase and to isolate those polynucleotides or genes which have a high similarity of sequence with that of the alanine racemase gene. They are also suitable for incorporation into so-called "arrays", "micro arrays" or "DNA chips" in order to detect and determine the corresponding polynucleotides.

Polynucleotides which comprise sequences according to the invention are furthermore suitable as primers for the preparation of DNA of genes which code for D-alanine racemase by the polymerase chain reaction (PCR).

Such oligonucleotides which serve as probes or primers comprise at least 25, 26, 27, 28, 29 or 30, preferably at least 20, 21, 22, 23 or 24 very particularly preferably at least 15, 16, 17, 18 or 19 successive nucleotides. Oligonucleotides with a length of at least 31, 32, 33, 34, 35, 36, 37, 38, 39 or 40 or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 8 or a fragment prepared therefrom and also those which are at least 70% to 80%, preferably at least 81% to 85%, particularly preferably at least 86% to 90%, and very particularly preferably at least 91%, 93%, 95%, 97% or 99% identical to the polynucleotide according to SEQ ID No. 8 or a fragment prepared therefrom.

"Polypeptides" are understood as meaning peptides or proteins which comprise two or more amino acids bonded via peptide bonds.

The polypeptides according to the invention include a polypeptide according to SEQ ID No. 9, in particular those with the biological activity of alanine racemase, and also those which are at least 70% to 80%, preferably at least 81% to 85%, particularly preferably at least 91%, 93%, 95%, 97% or 99% identical to the polypeptide according to SEQ ID No. 9 and have the activity mentioned.

The invention furthermore relates to a host-vector system comprising 1) a coryneform bacterium as the host, in which the chromosomal alr gene is present in attenuated, preferably eliminated, form, and 2) a plasmid which replicates in this host and carries at least the alr gene. The number of copies of the plasmid is at least 1 but not more than 1000, preferably at least 1 to 300, particularly preferably at least 1 to 100, and very particularly preferably at least 1 to 50. The host-vector system according to the invention has the advantage that it acts as a stabilization system and the addition of stabilizing or selectively acting substances, for example antibiotics, can therefore be reduced and optionally omitted.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

The invention also relates to processes for the fermentative preparation of chemical compounds, in particular L-amino acids, vitamins, nucleosides and nucleotides, using the host-vector system mentioned.

The following steps are carried out here:
a) fermentation of a coryneform microorganism which produces one or more desired chemical compounds and contains the alr host-vector system, optionally in absence of antibiotics in at least one fermentation stage,
b) concentration of this/these chemical compound(s) or the corresponding salt(s) in the medium or fermentation broth or in the cells of the coryneform microorganisms, and optionally
c) isolation of this/these chemical compound(s) and/or the corresponding salt(s), optionally together with some or all of the biomass and the dissolved constituents of the fermentation broth.

The desired chemical compounds include, preferably, L-amino acids, in particular the proteinogenic L-amino acids, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine and salts thereof.

Vitamins means, in particular, vitamin B1 (thiamine), vitamin B2 (riboflavin), vitamin B5 (pantothenic acid), vitamin B6 (pyridoxine), vitamin B12 (cyanocobalamin), nicotinic acid/nicotinamide, vitamin M (folic acid) and vitamin E (tocopherol) and salts thereof, pantothenic acid being preferred.

Nucleosides and nucleotides means, inter alia, S-adenosyl-methionine, inosine-5'-monophosphoric acid and guanosine-5'-monophosphoric acid and salts thereof.

The invention also relates to a process for the preparation of D-amino acids, in particular D-alanine and D-lysine, using suitable bacteria, in particular coryneform bacteria and Enterobacteriaceae, in which the nucleotide sequences of coryneform bacteria which code for the alr gene are enhanced, in particular over-expressed.

The following steps are in general carried out here:
a) culture of a bacterium in which the alr gene of a coryneform bacterium is present in enhanced form,
b) optionally isolation of some or all of the biomass,
c) optionally preparation of a cell extract or of a completely or partly purified enzyme from the biomass,
d) addition of the L-amino acid to the fermentation broth, or to the isolated biomass, or to the cell extract or to a completely or partly purified enzyme, optionally in a suitable buffer, and
e) isolation of the D-amino acid produced.

The term "enhancement" in this connection describes the increase in the intracellular activity of one or more enzymes in a microorganism which are coded by the corresponding DNA, for example by increasing the number of copies of the gene or genes, using a potent promoter or using a gene or allele which codes for a corresponding enzyme having a high activity, and optionally combining these measures.

The microorganisms which the present invention provides contain the host-vector system mentioned and are representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum*, are, for example, the known wild-type strains
*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020
and mutants or strains prepared therefrom which produce chemical compounds.

The invention furthermore provides bacteria, in particular coryneform bacteria and *Enterobacteriaceae*, in which the alr gene of coryneform bacteria is present in enhanced, in particular over-expressed, form.

The new alr gene from *C. glutamicum* which codes for the enzyme alanine racemase (EC No. 5.1.1.1) has been isolated.

The nucleotide sequences of the alr gene and the amino acid sequences of alanine racemase of various bacteria, such as, for example, *Bacillus subtilis, Mycobacterium smegmatis, Streptomyces coelicolor* or *Escherichia coli* are known and are available in publicly accessible databanks, such as, for example, that of European Molecular Biologies Laboratories (EMBL, Heidelberg, Germany) or that of the National Center for Biotechnology Information (NCBI, Bethesda, Md., USA) or that of the Swiss Institute of Bioinformatics (Swissprot, Geneva, Switzerland) or that of the Protein Information Resource Database (PIR, Washington, D.C., USA).

By comparing the amino acid sequences of the enzyme proteins of various bacteria, regions of a highly identical nature, that is to say so-called conserved protein regions, can be identified. Taking into account the codon use of Corynebacterium glutamicum (Malumbres et al., Gene 134, 15-24 (1993) I.B.R.), the nucleotide sequence of the corresponding DNA region can be concluded. Accordingly, synthetic oligonucleotides can in turn be synthesized and employed as primers for amplification of the corresponding chromosomal DNA segments by means of the polymerase chain reaction (PCR). Instructions for this are to found by the expert, inter alia, for example in the handbook by Gait: Oligonucleotide Synthesis: A Practical Approach (IRL Press, Oxford, UK, 1984) I.B.R. and in Newton and Graham: PCR (Spektrum Akademischer Verlag, Heidelberg, Germany, 1994) I.B.R. The DNA fragment of the alr gene obtained in this manner is then cloned by known methods and can be employed as a probe in the search for the complete gene, including its 5' and 3' flanks, in gene libraries by means of hybridization.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology 41: 255-260 (1991)) I.B.R. The hybridization preferably takes place under stringent conditions, that is to say only hybrids in which the probe and target sequence, i.e. the DNA fragments or genes treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996 I.B.R.).

A 5×SSC buffer at a temperature of approx. 50° C.-68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995 I.B.R.) a temperature of approx. 50° C.-68° C. being established. It is optionally possible to lower the salt concentration to 0.1×SSC. Polynucleotide fragments which are, for example, at least 70% or at least 80% or at least 90% to 95% or at least 96% to 99% identical to the sequence of the probe employed can be isolated by increasing the hybridization temperature stepwise from 50° C. to 68° C. in steps of approx. 1° C.-2° C. It is also possible to isolate polynucleotide fragments which are completely identical to the sequence of the probe employed. Further instructions on hybridization are obtainable on the market in the form of so-called kits (e.g. DIG Easy Hyb from Roche Diagnostics GmbH, Mannheim, Germany, Catalogue No. 1603558).

The setting up of gene libraries is described in generally known textbooks and handbooks. The textbook by Winnacker: Gene and Klone, Eine Einfuhrung in die Gentechnologie (Verlag Chemie, Weinheim, Germany, 1990) I.B.R., or the handbook by Sambrook et al.: Molecular Cloning, A Laboratory Manual (Cold Spring Harbor Laboratory Press, 1989) I.B.R. may be mentioned as an example. A well-known gene library is that of the *E. coli* K-12 strain W3110 set up in λ vectors by Kohara et al. (Cell 50, 495-508 (1987)) T.R.R. Bathe et al. (Molecular and General Genetics, 252:255-265, 1996) I.B.R. describe a gene library of *C. glutamicum* ATCC13032, which was set up with the aid of the cosmid vector SuperCos I (Wahl et al., 1987, Proceedings of the National Academy of Sciences USA, 84:2160-2164 I.B.R.) in the *E. coli* K-12 strain NM554 (Raleigh et al., 1988, Nucleic Acids Research 16:1563-1575 I.B.R.).

Bormann et al. (Molecular Microbiology 6(3), 317-326)) (1992)) I.B.R. in turn describe a gene library of *C. glutamicum* ATCC13032 using the cosmid pHC79 (Hohn and Collins, 1980, Gene 11, 291-298 I.B.R.).

To prepare a gene library of *C. glutamicum* in *E. coli* it is also possible to use plasmids such as pBR322 (Bolivar, 1979, Life Sciences, 25, 807-818 I.B.R.) or pUC9 (Vieira et al., 1982, Gene, 19:259-268 I.B.R.). Suitable hosts are, in particular, those *E. coli* strains which are restriction- and recombination-defective, such as, for example, the strain DH5αmcr, which has been described by Grant et al. (Proceedings of the National Academy of Sciences USA, 87 (1990) 4645-4649) I.B.R. The long DNA fragments cloned with the aid of cosmids or other λ vectors can then in turn be subcloned and subsequently sequenced in the usual vectors which are suitable for DNA sequencing, such as is described e.g. by Sanger et al. (Proceedings of the National Academy of Sciences of the United States of America, 74:5463-5467, 1977) I.B.R. or Frangeul et al. (Microbiology 145, 2625-2643 (1999)) I.B.R.

The resulting DNA sequences can then be investigated with known algorithms or sequence analysis programs, such as e.g. that of Staden (Nucleic Acids Research 14, 217-232 (1986)) I.B.R., that of Marck (Nucleic Acids Research 16, 1829-1836 (1988)) I.B.R. or the GCG program of Butler (Methods of Biochemical Analysis 39, 74-97 (1998)) I.B.R.

The invention provides the preparation of a host-vector system based on the alr gene for *Corynebacterium glutamicum*. The host-vector system comprises 1) a suitable host strain of Corynebacterium glutamicum in which the chromosomal air gene is present in attenuated form, and 2) a plasmid which replicates in this host and carries at least the alr gene. The number of copies of the plasmid is at least 1 but not more than 1000, preferably at least 1 to 300, particularly preferably at least 1 to 100, and very particularly preferably at least 1 to 50.

To achieve an attenuation, either the expression of the alr gene or the catalytic/regulatory properties of the enzyme protein can be reduced or eliminated. The two measures can optionally be combined.

The reduction in gene expression can take place by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in WO 96/15246 I.B.R., in Boyd and Murphy (Journal of Bacteriology 170: 5949 (1988)) I.B.R., in Voskuil and Chambliss (Nucleic Acids Research 26: 3548 (1998) I.B.R., in Jensen and Hammer (Biotechnology and Bioengineering 58: 191 (1998)) I.B.R., in Pátek et al. (Microbiology 142: 1297 (1996)) I.B.R., Vasicova et al. (Journal of Bacteriology 181: 6188 (1999)) I.B.R. and in known textbooks of genetics and molecular biology, such as e.g. the textbook by Knippers ("Molekulare Genetik", 6th edition, Georg Thieme Verlag, Stuttgart, Germany, 1995) I.B.R. or that by Winnacker ("Gene und Klone", VCH Verlagsgesellschaft, Weinheim, Germany, 1990) I.B.R.

Mutations which lead to a change or reduction in the catalytic properties of enzyme proteins are known from the prior art; examples which may be mentioned are the works by Qiu and Goodman (Journal of Biological Chemistry 272: 8611-8617 (1997)) I.B.R., Sugimoto et al. (Bioscience Biotechnology and Biochemistry 61: 1760-1762 (1997)) I.B.R. and Mockel ("Die Threonindehydratase aus *Corynebacterium glutamicum*: Aufhebung der allosterischen Regulation und Struktur des Enzyms", Reports from the Jülich Research Centre, Jül-2906, ISSN09442952, Julich, Germany, 1994) I.B.R. Summarizing descriptions can be found in known textbooks of genetics and molecular biology, such as e.g. that by Hagemann ("Allgemeine Genetik", Gustav Fischer Verlag, Stuttgart, 1986) I.B.R.

Possible mutations are transitions, transversions, insertions and deletions. Depending on the effect of the amino acid exchange on the enzyme activity, "missense mutations" or "nonsense mutations" are referred to. Insertions or deletions of at least one base pair (bp) in a gene lead to frame shift mutations, as a consequence of which incorrect amino acids are incorporated or translation is interrupted prematurely. If a stop codon is formed in the coding region as a consequence of the mutation, this also leads to a premature termination of the translation. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik", 6th edition, Georg Thieme Verlag, Stuttgart, Germany, 1995) I.B.R., that by Winnacker ("Gene and Klone", VCH Verlagsgesellschaft, Weinheim, Germany, 1990) I.B.R. or that by Hagemann ("Allgemeine Genetik", Gustav Fischer Verlag, Stuttgart, 1986) I.B.R.

An example of a mutated alr gene is the Δalr91 allele (deltaalr9l) shown in SEQ ID No. 12. It contains the 5' and the 3' region of the alr gene. A 75 by long section of the coding region is missing (deletion).

The mutation in the alr gene can be incorporated into suitable strains by gene or allele replacement.

A common method of mutating genes of *C. glutamicum* or of incorporating mutations in strains is the method of gene or allele replacement ("gene replacement", "allelic exchange" described by Schwarzer and PQhler (Bio/Technology 9, 84-87 (1991)) I.B.R. or by Schafer et al. (Gene 145, 69-73 (1994)) I.B.R.

In the method of "gene replacement", a mutation, such as e.g. a deletion, insertion or a base exchange, is established in vitro in the gene of interest. The allele prepared is in turn cloned in a vector which is not replicative for *C. glutamicum* and this is then transferred into the desired host of *C. glutamicum* by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch et al. (Microbiology 144, 915 - 927 (1998)) I.B.R. to eliminate the pyc gene of *C. glutamicum* by a deletion. Schafer et al. (Gene 145: 69-73 (1994)) I.B.R. used this method, for example, to incorporate a deletion in the hom-thrB gene region. In the same way, Kronemeyer et al. (Journal of Bacteriology 177: 1152-1158 (1995) I.B.R. inserted a deletion into the gluABCD gene region of *C. glutamicum*.

A deletion, insertion or integration or a base exchange can be incorporated into the alr gene in this manner. Strains which have an attenuated alr gene are auxotrophic for the amino acid D-alanine. An example of a host with an attenuated alr gene is the strain *Corynebacterium glutamicum* ATCC13032Δalr91 (ATCC13032deltaalr91), which carries the mutation shown in SEQ ID No. 12.

In a further step, an alr gene which is capable of functioning is incorporated into a plasmid by cloning methods known from the prior art. Suitable plasmids are those which are replicated in coryneform bacteria. Numerous known plasmid vectors, such as e.g. pZ1 (Menkel et al., Applied and Environmental Microbiology (1989) 64: 549-554 I.B.R.), pEKEx1 (Eikmanns et al., Gene 102:93-98 (1991) I.B.R.) or pHS2-1 (Sonnen et al., Gene 107:69-74 (1991) I.B.R.) are based on the cryptic plasmids pHM1519, pBL1 or pGA1 and can be used. Other plasmid vectors, such as e.g. those based on pCG4 (U.S. Pat. No. 4,489,160 I.B.R.), or pNG2 (Serwold-Davis et al., FEMS Microbiology Letters 66, 119-124 (1990) I.B.R.), or pAG1 (U.S. Pat. No. 5,158,891 I.B.R.), can be used in the same manner. An example of such a plasmid is the plasmid vector pSELF2000 shown in FIG. 5.

The plasmid which carries at least the alr gene is then transferred with the aid of transformation methods known from the prior art into a coryneform host which carries an attenuated alr gene in its chromosome. The transformant formed here requires no D-alanine. An example of such a host-vector system is the strain ATCC13032Δalr91 [pSELF2000].

A production gene, for example the panD gene (Dusch et al., Applied and Environmental Microbiology 65, 1530-1539 (1999)) I.B.R., which is of interest for the production of a chemical compound, for example the vitamin pantothenic acid, is in turn incorporated into the plasmid containing the alr gene, the resulting plasmid optionally carrying no gene which imparts resistance to antibiotics.

The resulting plasmid containing one or more production gene(s) is then incorporated by transformation or conjugation into the host which produces the particular chemical compound, the chromosomal alr gene of the host being attenuated, in particular eliminated.

The invention also provides the coryneform microorganisms prepared, which contain the host-vector system according to the invention which is dependent on the alr gene, and which can be cultured continuously or discontinuously in the batch process (batch culture) or in the fed batch (feed process) or repeated fed batch process (repetitive feed process) for the purpose of production of chemical compounds. A summary of known culture methods is described in the textbook by Chmiel (Bioprozesstechnik 1. Einführung in die Bioverfahrenstechnik (Gustav Fischer Verlag, Stuttgart, 1991)) I.B.R. or in the textbook by Storhas (Bioreaktoren and periphere Einrichtungen (Vieweg Verlag, Braunschweig/Wiesbaden, 1994)) I.B.R.

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus.

The culture medium must furthermore comprise salts of metals, such as, for example, magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam.

To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired chemical compound has formed. This target is usually reached within 10 hours to 160 hours.

It has been found that the addition of selectively acting substances to the medium, in particular antibiotics, can be reduced and optionally omitted with this invention. This means that in industrial processes, which in general are conducted over several stages, for example comprising shaking flask cultures, one or more prefermenters and the production fermenter, the addition of antibiotics in the production fermenter can be omitted in particular.

In the culture of strains which contain the host-vector system according to the invention, at least 3, preferably at least 6, particularly preferably at least 9, and very particularly preferably at least 12 generations are passed through in a nutrient medium which comprises no antibiotic.

It has furthermore been found in the present invention that the alanine racemase coded by the alr gene of Corynebacterium glutamicum can be employed for the preparation of D-alanine and D-valine. Bacteria, preferably coryneform bacteria and Enterobacteriaceae, in particular *Corynebacterium glutamicum* and *Escherichia coli*, in which the alr gene of *Corynebacterium glutamicum* is present in enhanced, in particular over-expressed, form are used for this.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of the culture. The expression is likewise improved by measures to prolong the life of the mRNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

The microorganisms prepared, in which the alanine racemase coded by the alr gene of coryneform bacteria is present in enhanced, in particular over-expressed, form, can be cultured continuously or discontinuously in the batch process (batch culture) or in the fed batch (feed process) or repeated fed batch process (repetitive feed process) for the purpose of obtaining the biomass. A summary of known culture methods is described in the textbook by Chmiel (Bioprozesstechnik 1. Einführung in die Bioverfahrenstechnik (Gustav Fischer Verlag, Stuttgart, 1991) I.B.R.) or in the textbook by Storhas (Bioreaktoren and periphere Einrichtungen (Vieweg Verlag, Braunschweig/Wiesbaden, 1994)) I.B.R.

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981) I.B.R.

The microorganisms cultured in this manner can be separated off from the culture broth by suitable separation processes, such as filtration, centrifugation, flocculation, precipitation or combinations of these. Descriptions of such procedures are to be found in the textbook "Mikrofiltration mit Membranen Grundlagen, Verfahren, Anwendungen" (Ripperger S., VCH Verlagsgesellschaft, Weilheim, Germany (1991) I.B.R.) or in the handbook "Bioseparations, Downstream Processing for Biotechnology" (Belter P. A., Cussler E. L., Hu Wei-Shou, John Wiley & Sons; New York (1988)) I.B.R. The concentrated and isolated biomass can be resuspended in aqueous buffer systems or organic solvents, such as, for example, acetone, methanol and acetonitrile, or mixtures of an aqueous buffer with an organic solvent and then employed for the preparation of the D-amino acid from the corresponding L-amino acid.

It is also possible to omit the concentration and isolation of the biomass and to introduce the L-amino acid directly into the fermentation broth and to isolate the D-amino acid produced from the fermentation broth.

If desired, the biomass prepared and obtained by the process described above can be employed for the preparation of a crude extract or cell extract or for the preparation of a completely or partly purified enzyme preparation.

By cell breakdown processes, for example by means of ultrasound, ball mills or high-pressure homogenizers, a cell extract can be prepared, which can then be employed directly for the conversion of the L-amino acid into the D-amino acid.

For the purpose of further purification, the cell extract obtained can be further processed by appropriate chromatographic or electrophoretic methods with the aim of purifying and isolating the alanine racemase. Processes for this are described in detail in the textbook by Chmiel
(Bioprozesstechnik 2. Angewandte Bioverfahrenstechnik (Gustav Fischer Verlag, Stuttgart, 1991)) I.B.R. and in the textbook "Industrielle Enzyme" (Heinz Ruttloff, Behr's Verlag GmbH & Co., Hamburg (1994)) I.B.R.

Further instructions and descriptions for such processes, which are also called biocatalysis, can be looked up in the textbook "Stereoselective Biocatalysis" (Ramesh N. Patel, Verlag Marcel Dekker, Inc. New York, Basel (2000)) I.B.R.

After the biomass or the cell extract or the purified enzyme has been separated off, the D-amino acid of the racemic chemical compound used or salts thereof can be obtained by suitable methods of working up, such as, for example, filtration, separation, reactive extraction, crystallization or drying.

It is also possible for the completely or partly purified alanine racemase to be bound to suitable carrier materials or embedded in a suitable matrix (immobilization). Possible carriers are, for example, polysaccharides, polyhydroxy compounds, silicates, silica gels, glasses, polyamides and polyamines. Agar, cellulose, alginate, gelatin and polyacryls, for example, can be used as the matrix. It is furthermore possible to enclose or encapsulate the enzyme in membranes. Instructions in this context are also to be found in the textbook "Industrielle Enzyme [Industrial Enzymes]" (Heinz Ruttloff, Behr's Verlag GmbH & Co., Hamburg (1994)) I.B.R.

Pure cultures of the following microorganism were deposited on 2. May 2001 at the Deutsche Sammlung für Mikroorganismen and Zellkulturen (DSMZ=German Collection of Microorganisms and Cell Cultures, Braunschweig, Germany) in accordance with the Budapest Treaty:

*Escherichia coli* DH5αMCR[pSAC-ALR81] as DSM 14277

*Corynebacterium glutamicum* ATCC13032Δalr91 as DSM 14280

*Corynebacterium glutamicum* ATCC13032Δalr91 [pSELF2000] as DSM 14279

The present invention is explained in more detail in the following with the aid of embodiment examples.

The following strains of bacteria were used:

*Corynebacterium glutamicum* LP-6 was deposited in the context of EP-B 0 472 869 I.B.R. at the Deutsche Sammlung von Mikroorganismen and Zellkulturen (DSMZ=German Collection of Microorganisms and Cell Cultures, Braunschweig, Germany) as DSM5816. The storage period of DSM5816 has been extended in accordance with rule 9.1 of the Budapest Treaty. DSM5816 has the following taxonomic features:

Cell form: Y-shaped branching

Peptidoglycan: meso-Diaminopimelic acid

Mycolic acids: *Corynebacterium mycolic* acids with a high similarity with DSM20300

Fatty acid pattern: typical fatty acid pattern of Corynebacterium with unbranched, saturated and unsaturated fatty acids with a high similarity with that of DSM20300.

Guanine+cytosine (G+C) content: 55.1%

16S rDNA sequence: 98.6% identical to DSM20300

DNA-DNA homology: 81.6% to DSM20300 *Corynebacterium glutamicum* ATCC13032 was obtained from the American Type Culture Collection (Manassas, Va., USA).

The general genetic working techniques mentioned in the following examples and the nutrient media used, such as, for example, LB agar, are described in the technical literature by Sambrook et al. (Molecular Cloning: A Laboratory Manual, Cold Spring Harbor Laboratory Press (1989)) I.B.R. The electrotransfer of plasmid DNA was carried out by the method of Liebl et al. (FEMS Microbiology Letters 65, 299-304 (1989)) Chromosomal DNA from *Corynebacterium glutamicum* was isolated by the method of Tauch et al. (Plasmid 34, 119-131 (1995)) I.B.R.

The sequencing of the DNA fragments described in the following examples was carried out by the dideoxy chain termination method of Sanger et al. (Proceedings of the National Academy of Sciences USA 74, 5463-5467 (1977)) I.B.R. The raw sequence data obtained were processed using the "STADEN software package" (Staden, Molecular Biotechnology 5, 233-241 (1996) I.B.R.). The computer-assisted coding region analyses were carried out with the "XNIP" program (Staden, Molecular Biotechnology 5, 233-241

(1996) I.B.R.). Further sequence analyses were carried out with the "BLAST programs" (Altschul et al., Nucleic Acids Research 25, 3389-3402 (1997)) I.B.R.

EXAMPLE 1

Isolation and Characterization of the Plasmid pTET3

For characterization of the plasmid pTET3, the bacteria strain Corynebacterium glutamicum LP-6 was cultured in LB medium and plasmid DNA was isolated in accordance with the instructions of the "NucleoBond Nucleic Acid Purification Kits and Cartridges User Manual (PT3167-1) (Clonetech Laboratories GmbH, Heidelberg, Germany, 1997) I.B.R. The plasmid DNA was separated in a 0.8% agarose gel and the plasmid band which corresponded to the plasmid pTET3 was re-isolated from the agarose gel. The working instructions for the experiment corresponded to the "QIAEX® II Handbook for DNA Extraction from Agarose Gels)" (Qiagen GmbH, Hilden, Germany, 1997) I.B.R. The re-isolated plasmid DNA of pTET3 was then digested, in each case individually and in combination, with the restriction enzymes AvrIII, MunI (New England Biolabs GmbH (Schwalbach, Germany), HpaI, ScaI, XbaI (Pharmacia Biotech Europe GmbH, Freiburg, Germany) and SpeI (Roche Diagnostics GmbH, Mannheim, Germany) in accordance with the manufacturers' instructions. The restriction batches were then separated in a 0.8% agarose gel. The restriction map of the plasmid pTET3 from Corynebacterium glutamicum LP-6 shown in FIG. 1 was determined by comparison of the DNA fragments obtained with DNA fragments of known length (DNA Molecular Weight Marker X, Roche Diagnostics GmbH, Mannheim, Germany).

EXAMPLE 2

Isolation and Sequencing of the Antibiotic Resistance Region of the Plasmid pTET3

For identification of antibiotic resistance regions on the plasmid pTET3, the resistant test strain Corynebacterium glutamicum LP-6 and the sensitive control strain Corynebacterium glutamicum ATCC13032 were first cultured in the presence and absence of various antibiotics and antibiotic concentrations in accordance with the instructions for experiments of the "National Committee of Clinical Laboratory Standards" (National Committee of Clinical Laboratory Standards, Methods for dilution antimicrobial susceptibility tests for bacteria that grow aerobically; Approved Standard, M7-A4 (1997)) I.B.R. The antibiotics required for this test, inter alia the antibiotic tetracycline, were obtained from Sigma-Aldrich Chemie GmbH (Deisenhofen, Germany) and employed in the concentrations stated in the "Approved Standards M7-A4". The nutrient medium required for this test, "MÜLLER-HINTON-Bouillon", was obtained from Merck KgaA (Darmstadt, Germany) and employed in accordance with the manufacturer's instructions. In accordance with the instructions of the "Approved Standards M7-A4", an inhibitory concentration could be determined for tetracycline (Table 1) and a resistance of the bacteria strain Corynebacterium glutamicum LP-6 to the antibiotic tetracycline could be identified. The plasmid DNA isolated from Corynebacterium glutamicum LP-6 with the aid of an alkaline lysis method ("NucleoBond Nucleic Acid Purification Kits and Cartridges User Manual (PT3167-1)", Clonetech Laboratories GmbH, Heidelberg, Germany, 1997 I.B.R.) was then transferred to Corynebacterium glutamicum ATCC13032 by electrotransfer.

In the primary selection on LB agar with 5 µg/ml tetracycline, selection was made direcLly for the presence of the tetracycline resistance identified. The presence of a plasmid in the transformed bacteria strain Corynebacterium glutamicum ATCC13032 was then demonstrated by an alkaline lysis method ("NucleoBond Nucleic Acid Purification Kits and Cartridges User Manual (PT3167-1)", Clonetech Laboratories GmbH, Heidelberg, Germany, 1997 I.B.R.). Restriction analyses of the plasmid DNA isolated and comparison of the fragment lengths obtained with DNA fragments of known length (DNA Molecular Weight Marker X, Roche Diagnostics GmbH, Mannheim, Germany) and with DNA fragments of the plasmid pTET3 showed that the transformed plasmid which imparts tetracycline resistance is the plasmid pTET3. The transformed strain was called Corynebacterium glutamicum ATCC13032[pTET3].

A renewed resistance test with the resistant test strain isolated, Corynebacterium glutamicum ATCC13032[pTET3], and the sensitive control strain Corynebacterium glutamicum ATCC13032 in the presence of various concentrations of the antibiotic tetracycline in accordance with the instructions for experiments of the "National Committee of Clinical Laboratory Standards" showed that the test strain Corynebacterium glutamicum ATCC13032[pTET3] has a resistance to this antibiotic (Table 1).

TABLE 1

Minimum inhibitory concentration (µg tetracycline per ml) of various Corynebacterium glutamicum strains

| Antibiotic | ATCC13032 | LP-6 | ATCC13032[pTET3] |
|---|---|---|---|
| Tetracycline | ≦0.75 | ≦12 | ≦12 |

≦ = The minimum inhibitory concentration is less than or equal to the value stated.

For further characterization of the tetracycline resistance of pTET3, the plasmid DNA was re-isolated from Corynebacterium glutamicum ATCC13032 [pTET3] with the aid of an alkaline lysis method ("NucleoBond Nucleic Acid Purification Kits and Cartridges User Manual (PT3167-1)", Clonetech Laboratories GmbH, Heidelberg, Germany, 1997 I.B.R.). The plasmid DNA was then cleaved with the restriction enzyme HindIII (Pharmacia Biotech Europe GmbH, Freiburg, Germany) and ligated in the Escherichia coli cloning vector pK18mob2 (Tauch et al., Plasmid 40, 126-139 (1998) I.B.R.).

The DNA restriction and the DNA ligation were carried out with the enzyme T4 DNA ligase (Roche Diagnostics GmbH, Mannheim, Germany) in accordance with the manufacturer's instructions. The ligation batch was then transferred by electroporation into the bacteria strain Escherichia coli DH5aMCR (Tauch et al., FEMS Microbiology Letters 123, 343-348 (1994) I.B.R.). After selection on LB agar supplemented with 5 µg/ml tetracycline, transformants with plasmid vectors which contained DNA sections from the plasmid pTET3 were obtained. The presence of the plasmids was demonstrated by an alkaline lysis method ("QIAprep® Miniprep Handbook for Purification of Plasmid DNA", Qiagen GmbH, Hilden, Germany, 1997 I.B.R.).

Restriction analyses of the plasmid DNA isolated and comparison of the fragment lengths obtained with DNA fragments of known length showed that the plasmid isolated, called pTET3-H9, consisted of the plasmid vector pK18mob2 and a DNA fragment from pTET3 approx. 4000 by in size. The plasmid vector pTET3-H9 originating from the cloning with the restriction enzyme HindIII imparts resistance to tetracycline (5 µg/ml) in Escherichia coli DH5αMCR.

Figure 2:
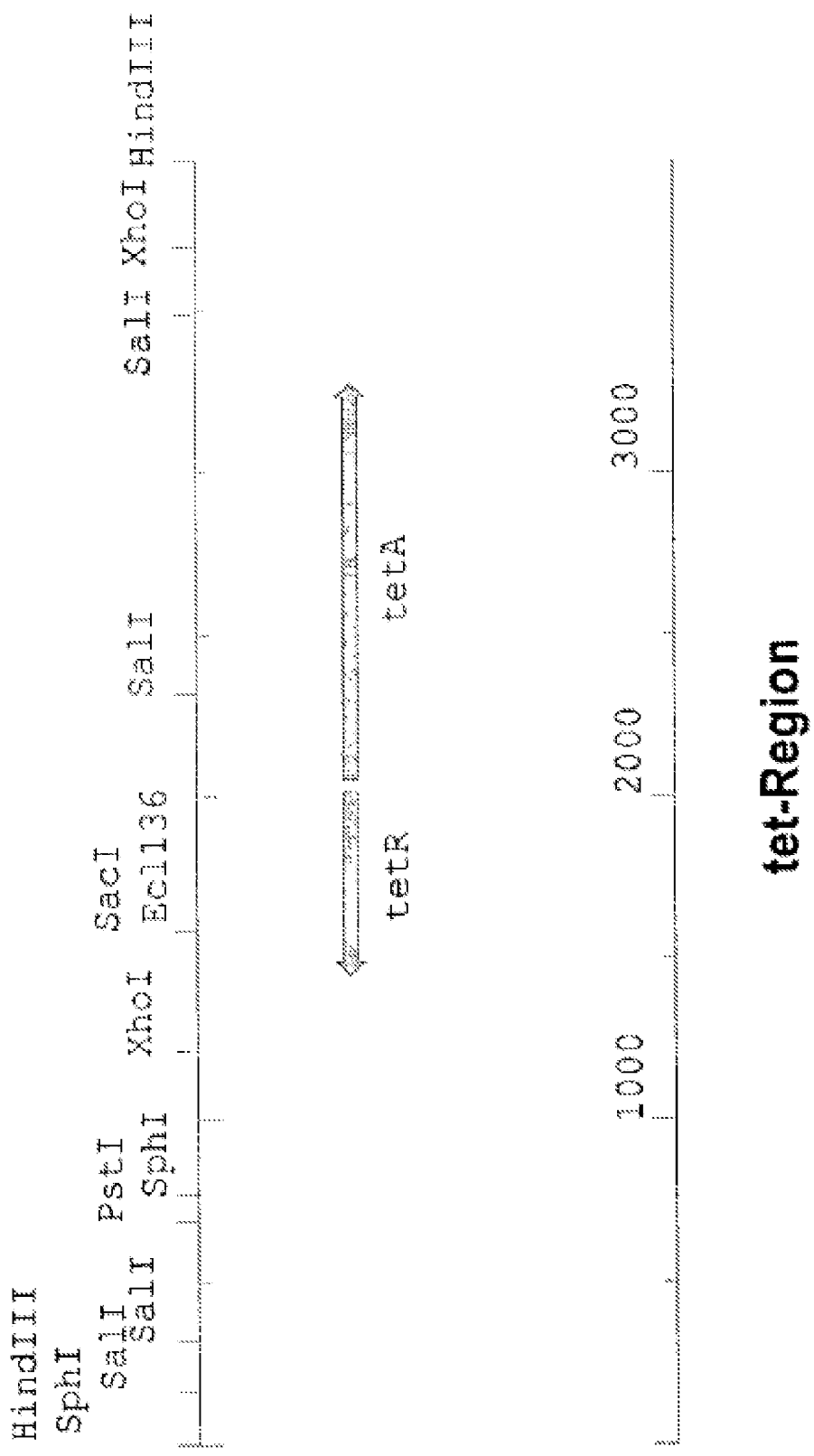
FIG. 2 is a map of the tetracycline resistance region of the plasmid pTET3.

For the double-stranded DNA sequencing of the DNA fragment of pTET3 approx. 400 by in size which imparts resistance to tetracycline, DNA of the plasmid pTET3-H9 was isolated in accordance with the instructions of the "QIAprep Miniprep Handbook for Purification of Plasmid DNA" (Qiagen GmbH, Hilden, Germany, 1997). After sequencing and analysis of the sequence, it was possible to determine two open reading frames (ORFs) on the DNA fragment sequenced. FIG. 2 shows a restriction map of the DNA regions of pTET3 sequenced and the position of the open reading frames (ORFs) identified. The analyses showed that ORF1 represents a tetR gene which codes for a tetracycline resistance repressor protein (TetR) and ORF2 represents a tetA gene which codes for a tetracycline resistance protein (TetA). The DNA sequence of the resistance region of pTET3 is reproduced in SEQ ID No. 1. The amino acid sequence, derived from the sequence data, of the tetracycline resistance protein (TetA) is shown in SEQ ID No. 2. The coding region of the tetR gene which codes for the tetracycline resistance repressor protein (TetR) is furthermore shown in SEQ ID No. 3, and the amino acid sequence derived is shown in SEQ ID No. 4.

EXAMPLE 3

Construction of the Plasmid Vector pSELF1-1

The plasmid vector pSELF1-1 was prepared from the known plasmid pGA1 (U.S. Pat. No. 5,175,108 I.B.R.) using the tetracycline resistance gene from pTET3 (See Example 1 and 2).

For this, total plasmid DNA of Corynebacterium glutamicum LP-6 was isolated by alkaline treatment of the bacteria cells ("NucleoBond Nucleic Acid Purification Kits and Cartridges User Manual (PT3167-1)", Clonetech Laboratories GmbH, Heidelberg, Germany, 1997 I.B.R.). The DNA preparation obtained was separated in a 0.8% agarose gel. The plasmid bands which corresponded to the plasmid pGA1 and the plasmid pTET3 were isolated from the agarose gel ("QIAEX® II Handbook for DNA Extraction from Agarose Gels", Qiagen GmbH, Hilden, Germany I.B.R.). Thereafter, the plasmid DNA of pGA1 isolated was cleaved with the restriction enzyme SalI (Pharmacia Biotech Europe GmbH, Freiburg, Germany) in accordance with the manufacturer's instructions. The plasmid DNA of pTET3 isolated was cleaved with the restriction enzyme XhoI (Pharmacia Biotech Europe GmbH, Freiburg, Germany).

Figure 3:
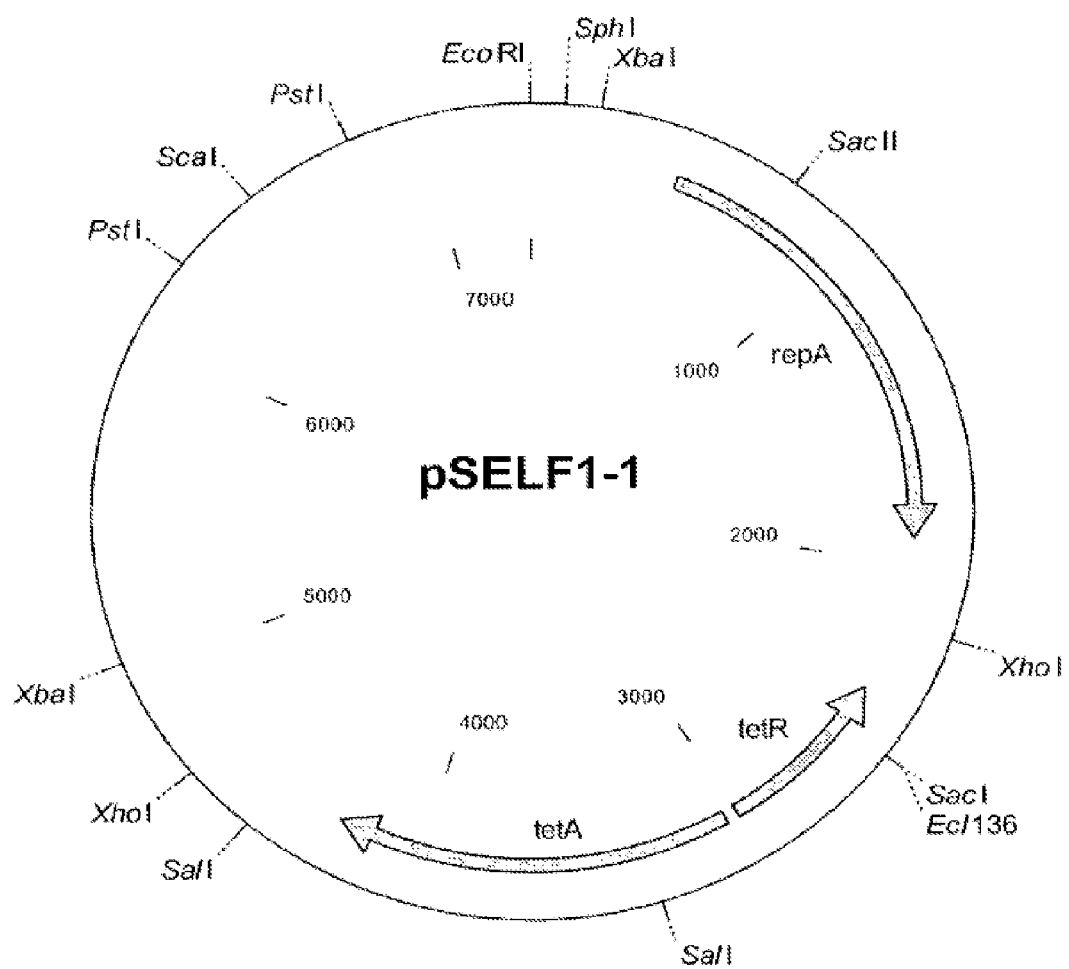
FIG. 3 is a map of the plasmid vector pSELF1-1.

The restriction batch of pTET3 was separated in 0.8% agarose gel and a DNA fragment approx. 2500 by in size, on which the tetracycline resistance region is located according to the DNA sequence data (Example 2), was re-isolated. The DNA fragment of pGA1 produced and the re-isolated DNA fragment of pTET3 were then ligated with one another by means of T4 DNA ligase (Roche Diagnostics GmbH, Mannheim, Germany) in accordance with the manufacturer's instructions. The ligation mixture was transferred into Corynebacterium glutamicum ATCC13032 by electroporation. Selection was carried out on LB agar with 5 µg/ml tetracycline. After incubation for 48 hours at 30° C., colonies which contained the new plasmid vector were isolated. The presence of the plasmid vector in the transformed bacteria cells was demonstrated by an alkaline lysis method ("QIAGEN Plasmid Mini Handbook for Plasmid Mini Kit", Qiagen GmbH, Hilden, Germany, 1997 I.B.R.). The plasmid isolated was called pSELF1-l. Restriction analyses of pSELF1-1 and comparison of the fragment lengths obtained with DNA fragments of known length gave the restriction map which is attached as FIG. 3.

By this construction route, plasmid pSELF1-1 comprises exclusively DNA fragments which originate from Corynebacterium glutamicum.

EXAMPLE 4

Identification of the Alr Gene from Corynebacterium Glutamicum

The alr gene from Corynebacterium glutamicum ATCC13032 was identified by means of a PCR method and chromosomal template DNA.

Conserved protein regions were first identified from a multiple comparison with amino acid sequences of known Alr proteins from Escherichia coli (GenBank Accession Number AE000478), Mycobacterium smegmatis (GenBank Accession Number U70872), Mycobacterium leprae (GenBank Accession Number U00020), Bacillus subtilis (GenBank Accession Number AB001488) and Streptomyces coelicolor (GenBank Accession Number AL031317) using the ALIGN computer program (Myers and Miller, Computer Application in Bioscience 4, 11-17 (1988) I.B.R.). The conserved protein regions were then identified at the DNA level in the nucleotide sequences from Mycobacterium smegmatis (GenBank Accession Number U70872), Mycobacterium leprae (GenBank Accession Number U00020) and Escherichia coli (GenBank Accession Number AE000478) and likewise compared with one another with the ALIGN computer program.

Taking into account the codon use of Corynebacterium glutamicum (Malumbres et al., Gene 134, 15-24 (1993)), the following oligonucleotide primers for the conserved DNA regions were prepared and used (See also SEQ ID No. 5 and 6):

```
                                    SEQ ID NO: 5
ALR1-1:     5'-CTGATGGCGGTGGTSAAGGC-3'

SEQ ID NO: 6
ALR4-1:     5'-CGAACTGATCCATGCATAAGCG-3'.
```

A PCR reaction was carried out with the primers ALR1-1 and ALR4-1 (ARK Scientific GmbH, Darmstadt, Germany) and chromosomal template DNA from Corynebacterium glutamicum ATCC13032 in a PCT-100 thermocycler (MJ Research Inc., Watertown, USA). The amplification was carried out with Taq DNA polymerase (Qiagen, Hilden, Germany) in accordance with the manufacturer's instructions in a total reaction volume of 50 µl. The PCR conditions were established as follows:

2 minutes initial running at 94° C., 90 seconds denaturing at 94° C., 45 seconds primer annealing at 61° C. and 90 seconds extension at 72° C. The amplification steps were repeated 35 times and concluded with an extension step of 5 minutes at 72° C. From the PCR reaction, 3 µl were separated in a 0.8% agarose gel with a DNA length standard (DNA Molecular Weight Marker X, Roche Diagnostics GmbH, Mannheim, Germany) and the amplification of a DNA fragment approx. 830 by in size was demonstrated.

The PCR product obtained was then cloned in the vector pCR2.1-TOPO® (Invitrogen BV, Groningen, The Netherlands). Cloning was carried out in accordance with the manufacturer's instructions ("TOPO® TA Cloning Instruction Manual, Version H", Invitrogen BV, Groningen, The Netherlands, 1999 I.B.R.). Selection of the clones was carried out on antibiotic medium no. 3 (Oxoid GmbH, Wesel, Germany) supplemented with 25 µg/ml kanamycin and 20 µg/ml X-Gal (5-bromo-4-chloro-3-indolyl-β-galoactopyranoside; Biosolve By, Valkenswaard, The Netherlands). Plasmid DNA was isolated from recombinant clones in accordance with the instructions of the "QIAprep® Miniprep Handbook for Purification of Plasmid DNA" (Qiagen GmbH, Hilden, Germany, 1997 I.B.R.) and cleaved with the restriction enzyme EcoRI (Pharmacia Biotech Europe GmbH, Freiburg, Germany,). Separation of the cleavage batch in 0.8% agarose gel showed that the PCR product approx. 830 by in size was cloned. The resulting plasmid was called pALR14-12.

The plasmid DNA of pALR14-12 isolated was furthermore employed for DNA sequencing with the universal reverse primer system (Invitrogen, Groningen, The Netherlands) and the chain termination method of Sanger et al. (Proceedings of the National Academy of Sciences USA 74, 5463-5467 (1977)). The resulting DNA sequence is shown in SEQ ID No. 7. The DNA sequence was leveled with the BLAST programs against the databank of the "National Center for Biotechnology Information" (NCBI, Bethesda, USA). The DNA amplified with the primers ALR1-1 and ALR4-1 showed, at the derived protein level, inter alia, homology with the Alr protein from *Mycobacterium tuberculosis* (GenBank Accession Number AL123456).

EXAMPLE 5

Sequence Analysis of the Alr Gene from *Corynebacterium Glutamicum*

The plasmid pALR14-12 was isolated in accordance with the instructions of the "QIAprep Miniprep Handbook for Purification of Plasmid DNA" (Qiagen GmbH, Hilden, Germany, 1997) and cleaved with the restriction enzyme EcoRI (Pharmacia Biotech Europe GmbH, Freiburg, Germany). The cleavage batch was separated in 0.8% agarose gel. The EcoRI fragment of pALR14-12 approx. 830 by in size was isolated from the agarose gel ("QIAEX® II Handbook for DNA Extraction from Agarose Gels", Qiagen GmbH, Hilden, Germany I.B.R.) and marked with the DNA Labeling and Detection Kit (Roche Diagnostics GmbH, Mannheim, Germany) in accordance with the manufacturer's instructions. This marked DNA probe was hybridized against the cosmid library of *Corynebacterium glutamicum* ATCC13032 described by Bathe et al. (Molecular and General Genetics 252, 255-265 (1996)) I.B.R. The hybridization was also carried out in accordance with the manufacturer's instruction with the DNA Labeling and Detection Kit (Roche Diagnostics GmbH, Mannheim, Germany). A hybridizing cosmid was identified in the cosmid library by this method. This cosmid was isolated in accordance with the instructions of the "QIAprep® Miniprep Handbook for Purification of Plasmid DNA" (Qiagen GmbH, Hilden, Germany, 1997 I.B.R.) and employed for DNA sequencing.

Figure 4:
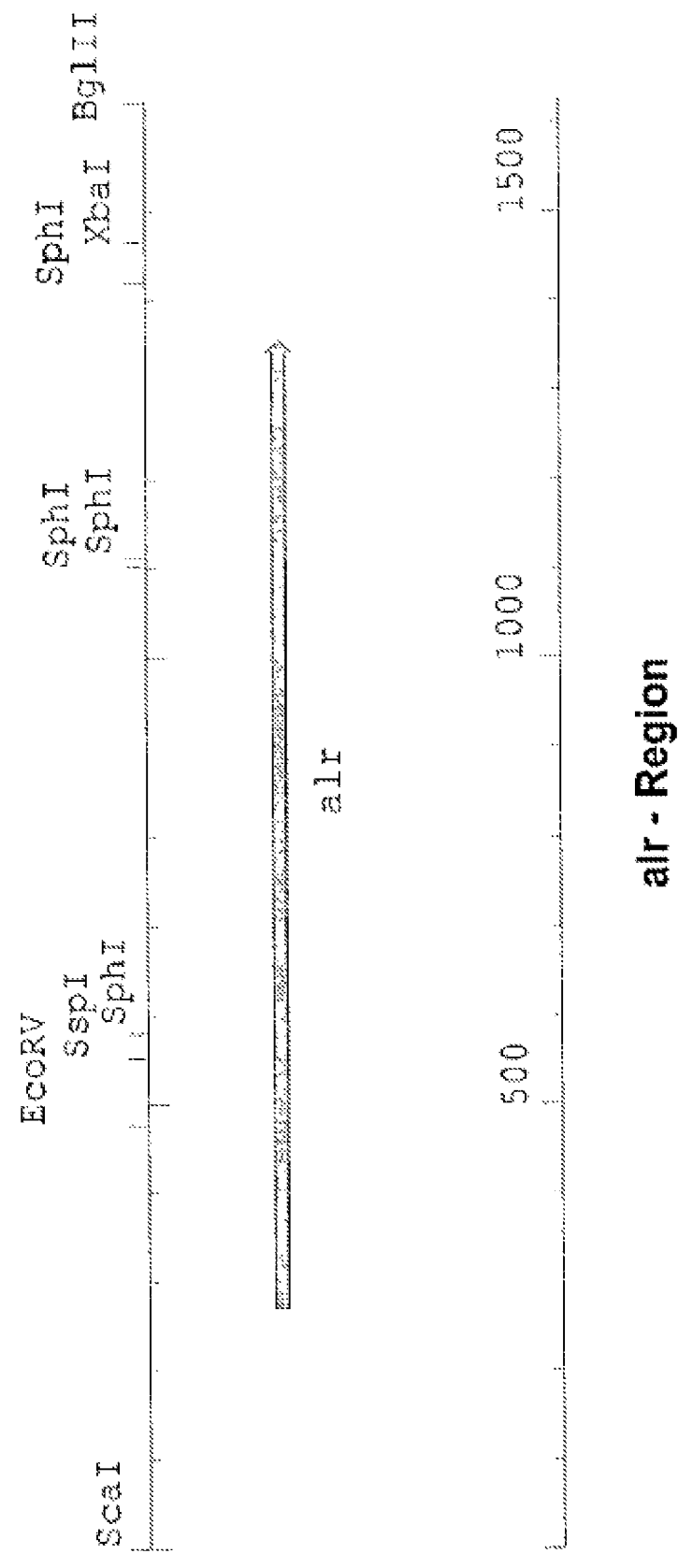
FIG. 4 is a map of the alr gene region.

Starting from the sequence of the identified amplification product, contained in plasmid pALR14-12, of the alr DNA fragment (Example 4), DNA sequencing of the entire alr gene was carried out by the primer walking method (Frangeul et al., Microbiology 145, 2625-2634(1999)). A continuous DNA sequence approx. 1.8 kb in size which corresponds to an ScaI-BglII fragment from the chromosome of *Corynebacterium glutamicum* ATCC13032 was obtained in this manner. A restriction map of the DNA region sequenced is shown in FIG. 4. The DNA sequence determined is shown in SEQ ID No. 8. Analysis of the coding probability of the DNA region sequenced showed a coding region present in complete form, the protein sequence of which (See SEQ ID No. 9) has a high homology with known Alr proteins in the NCBI databank (Bethesda, USA). This coding region was called the alr gene (FIG. 4).

EXAMPLE 6

Construction and Phenotypic Characterization of an Alr Mutant of *Corynebacterium Glutamicum*

The alr gene region was amplified with the primers

```
RACA: 5'-GGTATCTGCGGCATGCTCAA-3'    (SEQ ID No. 10)
and
RACB: 5'-TCATATCGCCTACCAGCACG-3'    (SEQ ID No. 11)
```

(ARK Scientific GmbH, Darmstadt, Germany) derived from the DNA sequence (SEQ ID No. 8) and with chromosomal template DNA from *Corynebacterium glutamicum* ATCC13032. The PCR reaction was carried out in a PCT-100 thermocycler (MJ Research Inc., Watertown, USA). The amplification was carried out with Taq DNA polymerase (Qiagen, Hilden, Germany) in accordance with the manufacturer's instructions in a total reaction volume of 50 µl. The PCR conditions were established as follows:

2 minutes initial running at 94° C., 90 seconds denaturing at 94° C., 45 seconds primer annealing at 57° C. and 90 seconds extension at 72° C. The amplification was repeated 35 times and concluded with an extension step of 5 minutes at 72° C. From the PCR reaction, 3 µwere separated in a 0.8% agarose gel with a DNA length standard (DNA Molecular Weight Marker X, Roche Diagnostics GmbH, Mannheim, Germany) and the amplification of a DNA fragment approx. 1.3 kb in size was demonstrated in this way.

The PCR product obtained was then cloned in the vector pCR2.1-TOPO® (Invitrogen BV, Groningen, The Netherlands). Cloning was carried out in accordance with the manufacturer's instructions ("TOPO® TA Cloning Instruction Manual, Version H", Invitrogen BV, Groningen, The Netherlands, 1999 I.B.R.). Selection of the clones was carried out on antibiotic medium no. 3 (Oxoid GmbH, Wesel, Germany) with 25 µg/ml kanamycin and 20 µg/ml X-Gal (Biosolve BV, Valkenswaard, The Netherlands). Plasmid DNA was isolated from recombinant clones in accordance with the instructions of the "QIAprep® Miniprep Handbook for Purification of Plasmid DNA" (Qiagen GmbH, Hilden, Germany, 1997 I.B.R.) and cleaved with the restriction enzyme EcoRI (Pharmacia Biotech Europe GmbH, Freiburg, Germany). Separation of the cleavage batch in 0.8% agarose gel showed that the PCR product approx. 1.3 kb in size was cloned. The resulting plasmid was called pALR5.

The DNA fragment approx. 1.3 kb in size was excised from the plasmid pALR5 with the restriction enzyme EcoRI (Pharmacia Biotech Europe GmbH, Freiburg, Germany) and cloned in the vector pK18mobsacB (Schafer et al., Gene 145, 69-73 (1994) I.B.R.). The DNA restriction and the DNA ligation were carried out with the enzyme T4 DNA ligase (Roche Diagnostics GmbH, Mannheim, Germany) in accordance with the manufacturer's instructions. The ligation batch was then transferred by electroporation into the bacteria strain *Escherichia coli* DH5αMCR (Tauch et al., FEMS Microbiology Letters 123, 343-348 (1994) I.B.R.) and selection was carried out on antibiotic medium no. 3 (Oxoid GmbH, Wesel, Germany) with 25 µg/ml kanamycin and 20 µg/ml X-Gal (Biosolve BV, Valkenswaard, The Netherlands).

Figure 5:
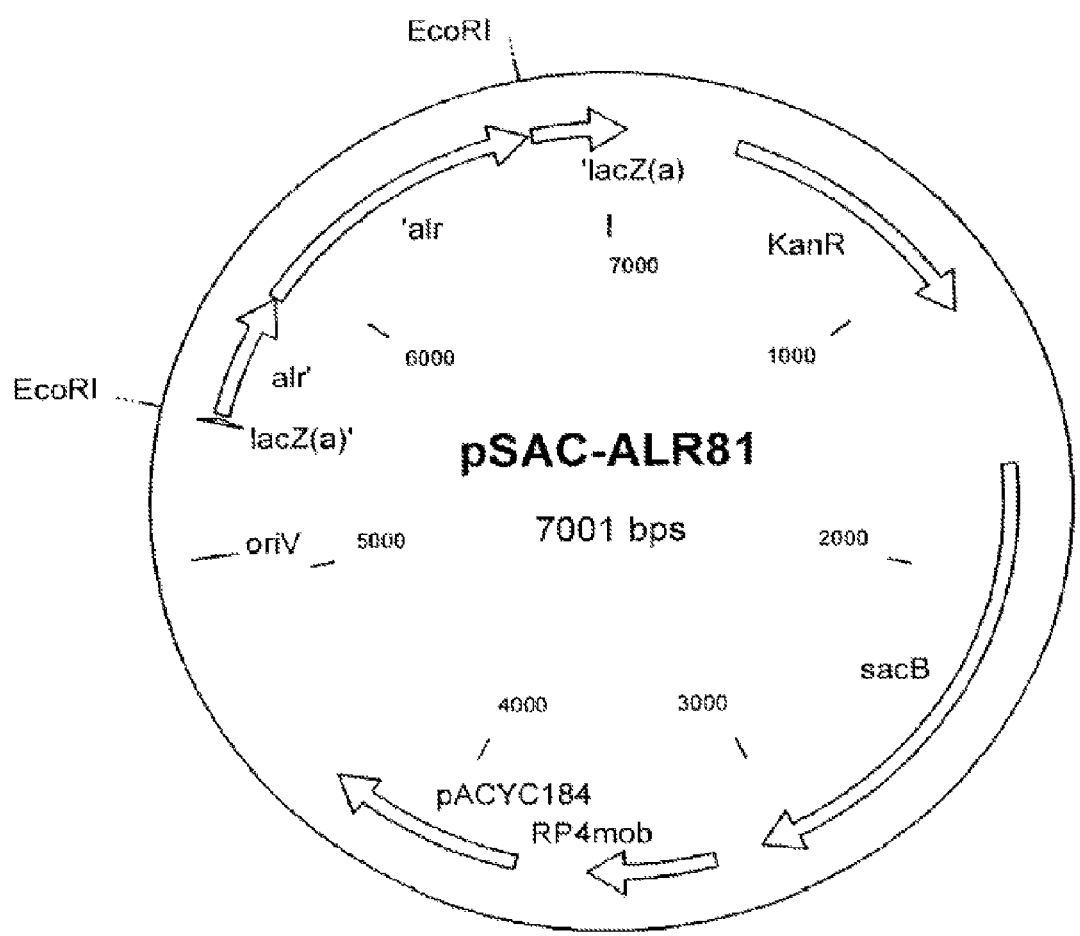
FIG. 5 is a map of the plasmid pSAC-alr81.

The presence of plasmids in the transformed bacteria cells was demonstrated by an alkaline lysis method ("QIAprep® Miniprep Handbook for Purification of Plasmid DNA", Qiagen GmbH, Hilden, Germany, 1997 I.B.R.). Restriction analyses of the plasmid DNA isolated and comparison of the fragment lengths obtained with DNA fragments of known length showed that the plasmid isolated comprised the plasmid vector pK18mobsacB and the DNA fragment from pALR5 approx. 1.3 kb in size. A deletion was then introduced in the same manner into the resulting plasmid with the enzymes EcoRV and SspI (Pharmacia Biotech Europe GmbH, Freiburg, Germany). The resulting plasmid was called pSAC-ALR81 and is shown in FIG. 5. The sequence of the alr allele contained in this plasmid and designated Δalr91 is shown in SEQ ID No. 12.

The deletion construct pSAC-ALR81 was transferred to Corynebacterium glutamicum ATCC13032 by electroporation. Selection of the plasmid integration was carried out on LB agar supplemented with 25 µg/ml kanamycin. Further construction of the alr deletion mutant was carried out in accordance with the test instructions of Schafer et al. (Gene 145, 69-73 (1994)) I.B.R. An individual colony of the integrant strain was cultured for 15 hours in 10 ml LB medium supplemented with 0.4 g/l D-alanine and then plated out on LB agar supplemented with 0.4 g/l D-alanine and 100 g/l sucrose. After incubation of the agar plates for 15 hours at 30° C., individual colonies were transferred in parallel to the three test nutrient media LB agar+0.4 g/l D-alanine, LB agar+0.4 g/l D-alanine+25 µg/ml kanamycin and LB agar. After a further incubation of 20 hours at 30° C., recombinant clone which grow only on LB agar with addition of 0.4 g/l D-alanine were identified. These clones carry the deletion designated Δalr91 in the alr gene.

To demonstrate the Δalr91 deletion in the chromosome of Corynebacterium glutamicum ATCC13032, chromosomal DNA was isolated from a clone and employed as template DNA in a PCR reaction alongside a control with chromosomal DNA from the wild-type Corynebacterium glutamicum ATCC13032. The PCR primers were derived from DNA sequence determined for the alr gene, shown in SEQ ID No. 8:

```
ALRD1:   5'-GGTTGGTGGCACAATAGTTC-3' (SEQ ID No. 13)

ALRD2:   5'-GGTGAGTTGCATACGTGGTT-3' (SEQ ID No. 14)
```

(ARK Scientific GmbH, Darmstadt Germany). The PCR reaction was carried out with a PCT-100 thermocycler (MJ Research Inc., Watertown, USA). The amplification was carried out with Taq DNA polymerase (Qiagen, Hilden, Germany) in accordance with the manufacturer's instructions in a total reaction volume of 50 µl. The PCR conditions were established as follows:

2 minutes initial running at 94° C., 90 seconds denaturing at 94° C., 45 seconds primer annealing at 55° C. and 90 seconds extension at 72° C. The amplification steps were repeated 35 times and concluded with an extension step of 5 minutes at 72° C. From the PCR reaction, 3 µwere separated in a 0.8% agarose gel with a DNA length standard (DNA Molecular Weight Marker X, Roche Diagnostics GmbH, Mannheim, Germany) and the amplification of a DNA fragment approx. 620 by in size was demonstrated in this way.

The PCR amplification product was then digested with the enzymes EcoRV and SspI (Pharmacia Biotech Europe GmbH, Freiburg, Germany). The restriction batches were separated in 0.8% agarose gel with a DNA length standard (DNA Molecular Weight Marker X, Roche Diagnostics GmbH, Mannheim, Germany) and the absence of the restriction cleavage sites for the enzymes EcoRV and SspI was demonstrated in this manner. This result confirms the incorporation of the Δalr91 deletion into the air gene. The strain obtained and tested in this manner was called Corynebacterium glutamicum ATCC13032Δalr91.

EXAMPLE 7

Construction of a Plasmid Vector for Antibiotic-free Selection in Corynebacterium Glutamicum ATCC13032Δalr91

To utilize the alr gene for developing cloning vectors for Corynebacterium glutamicum, the complete alr gene was isolated from the chromosome of Corynebacterium glutamicum ATCC13032 by the PCR technique. The primer combination employed was the oligonucleotides

```
RACF:   5'-GATGCCTGCCGAATTCTTCC-3'  (SEQ ID No. 15)
and

RACH:   5'-TTACGCCGCCGAGAATCTGA-3'  (SEQ ID No. 16)
```

(ARK Scientific GmbH, Darmstadt, Germany). The PCR reaction was carried out in a PCT-100 thermocycler (MJ Research, Watertown, Mass., USA). The amplification was carried out with Taq DNA polymerase (Qiagen, Hilden, Germany) in accordance with the manufacturer's instructions in a total reaction volume of 50 µl. The PCR conditions were established as follows:

2 minutes initial running at 94° C., 90 seconds denaturing at 94° C., 45 seconds primer annealing at 57° C. and 90 seconds extension at 72° C. The amplification was repeated 35 times and concluded with an extension step of 5 minutes at 72° C. From the PCR reaction, 3 µl were separated in a 0.8% agarose gel with a DNA length standard (DNA Molecular Weight Marker X, Roche Diagnostics GmbH, Mannheim, Germany) and the amplification of a DNA fragment approx. 1.6 kb in size was demonstrated in this way.

Figure 6:
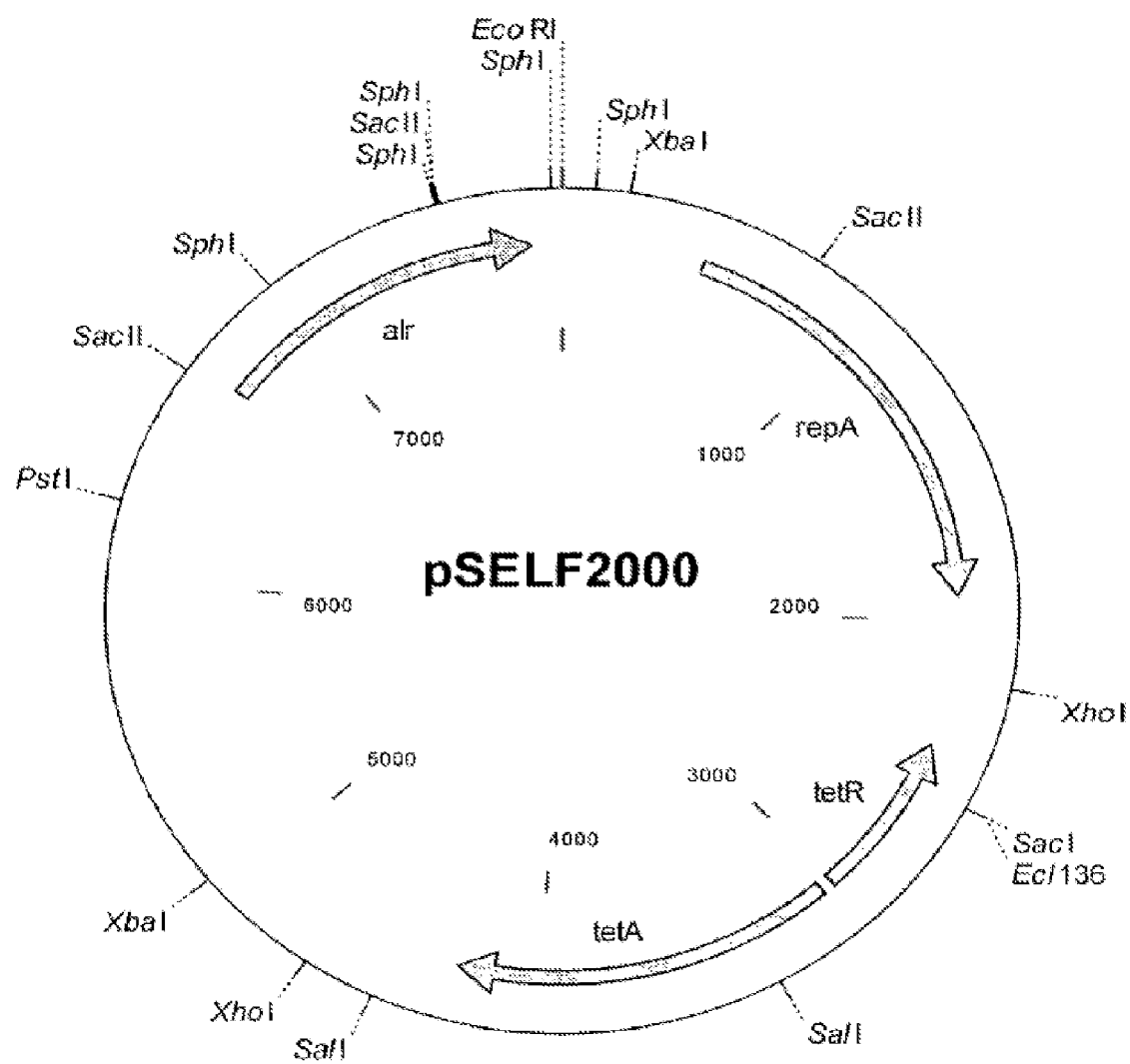
FIG. 6 is a map of the plasmid vector pSELF2000.

The amplified DNA was then subsequently cleaved with the enzymes EcoRI and ScaI (Pharmacia Biotech Europe GmbH, Freiburg, Germany) and cloned in the vector pSELF1-1 (Example 3), which had likewise been cleaved with the enzymes EcoRI and ScaI. The ligation batch was transferred by the method of Liebl et al. (FEMS Microbiology Letters 65, 299-304 (1989)) I.B.R. into the recipient strain Corynebacterium glutamicum ATCC13032Δalr91 (Example 6). Selection was carried out on LB medium with 5 µg/ml tetracycline. The plasmid transformation which had taken place was demonstrated by an alkaline lysis method ("QIAGEN Plasmid Mini Handbook for Plasmid Mini Kit", Qiagen GmbH, Hilden, Germany, 1997 I.B.R.) and subsequent agarose gel electrophoresis. The vector constructed consists of the EcoRI-ScaI fragment of pSELF1-1 and the PCR amplification product of the alr gene from Corynebacterium glutamicum ATCC13032 and was called pSELF2000. A restriction map of the plasmid pSELF2000 is attached in FIG. 6.

To test the properties of the plasmid pSELF2000, 1 µg of the plasmid DNA isolated was transferred to Corynebacterium glutamicum ATCC13032Δalr91 (Example 6) by electroporation. Selection was carried out in parallel on LB agar supplemented with 5 µg/ml tetracycline and 0.4 g/l D-alanine and on LB agar. The selection agar plates were incubated for 20 hours at 30° C. The number of clones obtained was then counted. The result is shown in Table 2. To demonstrate the transformation, the plasmid DNA was isolated from in each case 10 colonies by alkaline lysis ("QIAGEN Plasmid Mini Handbook for Plasmid Mini Kit", Qiagen GmbH, Hilden, Germany, 1997 I.B.R.) and detected in 0.8% agarose gel.

The plasmid pSELF2000 allows selection without the use of antibiotics. The number of clones after an electrotransfer of the plasmid and subsequent selection on antibiotic-free LB agar is higher than in the case of selection with the aid of tetracycline.

Figure 7:
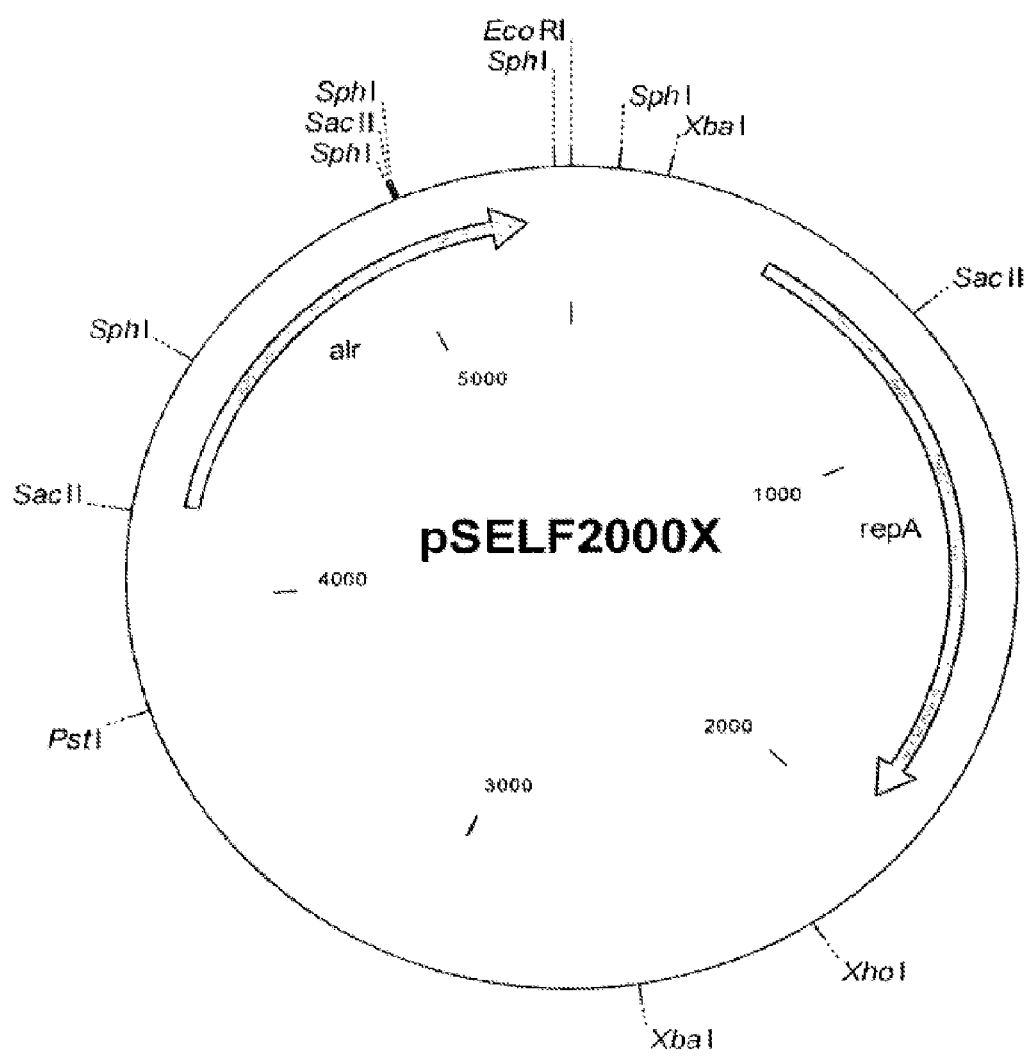
FIG. 7 is a map of the plasmid vector pSELF2000X.

The plasmid pSELF2000 was furthermore digested with the restriction enzyme XhoI (Pharmacia Biotech Europe GmbH, Freiburg, Germany) in order to remove the antibiotic resistance region. The ligation batch was transformed to Corynebacterium glutamicum ATCC13032Δalr91 and selection was carried out on LB agar. The resulting plasmid vector was called pSELF2000X. A map of pSELF2000X is shown in FIG. 7. To test the properties of the plasmid pSELF2000X, 1 μg of the plasmid DNA isolated was transferred to Corynebacterium glutamicum Δalr91 (Example 6) by electroporation. Selection was carried out on LB medium. The selection agar plates were incubated for 20 hours at 30° C. The number of colonies obtained was then counted. Approximately 15 generations are passed through during multiplication of a transformed cell to a colony. The result is shown in Table 2. To demonstrate the transformation which had taken place, the plasmid DNA was isolated from 10 colonies by alkaline lysis ("QIAGEN Plasmid Mini Handbook for Plasmid Mini Kit", Qiagen GmbH, Hilden, Germany, 1997 I.B.R.) and detected in 0.8% agarose gel.

The plasmid pSELF2000X comprises exclusively DNA fragments from Corynebacterium glutamicum and carries no antibiotic resistance gene, but is suitable for selection in Corynebacterium glutamicum ATCC13032Δalr91.

TABLE 2

Transformation of Corynebacterium glutamicum ATCC13032Δalr91 (transformants per μg plasmid DNA)

| Plasmid | Selection medium | Transformants per μg plasmid DNA |
|---|---|---|
| pSELF2000 | LB agar + 5 μg/ml tetracycline | $6.8 \times 10^6$ |
| pSELF2000 | LB | $1.5 \times 10^7$ |
| pSELF2000X | LB | $2.9 \times 10^7$ |

EXAMPLE 8

Cloning of the panD Gene from Corynebacterium Glutamicum ATCC13032

The complete panD gene of Corynebacterium glutamicum ATCC 13032 was amplified by PCR with chromosomal template DNA with the aid of the known DNA sequence (Dusch et al., Applied and Environmental Microbiology 65, 1530-1539(1999) I.B.R.). The primer combination employed was the oligonucleotides

```
PAA1:   5'-AGTACTAATTGCGGTGGCAG-3' (SEQ ID No. 17)
and

PAMOD:  5'-CGTCATCGTTGTCGACAGTG-3' (SEQ ID No. 18)
```

(ARK Scientific GmbH, Darmstadt, Germany). The primer PAMOD was modified with respect to the chromosomal DNA sequence of Corynebacterium glutamicum ATCC 13032 by insertion of a recognition sequence for the restriction enzyme SalI. The subsequent PCR reaction was carried out in a PCT-100 thermocycler (MJ Research, Watertown, Mass., USA). The amplification was carried out with Taq DNA polymerase (Qiagen, Hilden, Germany) in accordance with the manufacturer's instructions in a total reaction volume of 50 μl. The PCR conditions were established as follows:

2 minutes initial running at 94° C., 90 seconds denaturing at 94° C., 45 seconds primer annealing at 55° C. and 90 seconds extension at 72° C. The amplification was repeated 35 times and concluded with an extension step of 5 minutes at 72° C. From the PCR reaction, 8 μl were separated in a 0.8% agarose gel with a DNA length standard (DNA Molecular Weight Marker X, Roche Diagnostics GmbH, Mannheim, Germany) and the amplification of a DNA fragment approx. 1.1 kb in size was demonstrated in this way.

Figure 8:
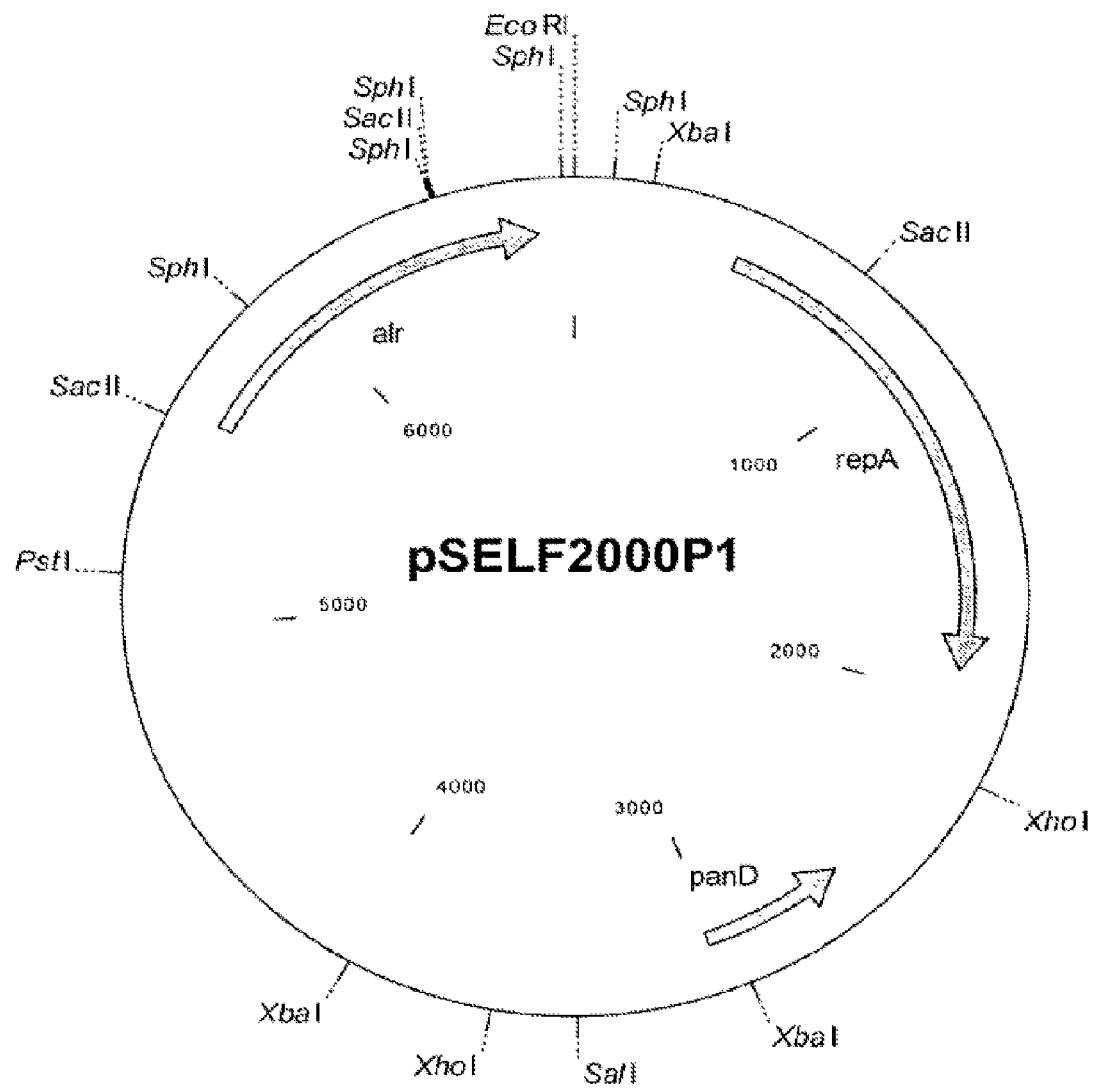
FIG. 8 is a map of the plasmid vector pSELF2000P1.

For cloning of the amplification product, the DNA fragment approx. 1.1 kb in size was re-isolated from the agarose gel with the "QIAEX® II Gel Extraction Kit" in accordance with the manufacturer's instructions ("QIAEX® II Handbook for DNA Extraction from Agarose Gels", Qiagen GmbH, Hilden, Germany, 1997 I.B.R.) and cleaved with the two restriction enzymes SalI and NaeI (Pharmacia Biotech Europe GmbH, Freiburg, Germany). The vector pSELF2000 (Example 7) was also cleaved with the restriction enzymes SalI (Pharmacia Biotech Europe GmbH, Freiburg, Germany) and Ec1136II (MBI Fermentas GmbH, St. Leon-Rot, Germany). The cleavage batches were ligated with one another with T4 DNA ligase (Roche Diagnostics GmbH, Mannheim, Germany) in accordance with the manufacturer's instructions. The ligation batch was transferred by the method of Liebl et al. (FEMS Microbiology Letters 65, 299-304 (1989)) I.B.R. into the recipient strain Corynebacterium glutamicum ATCC13032Δalr91 (Example 6). Selection was carried out on LB agar. The plasmid transformation which had taken place was demonstrated by an alkaline lysis method ("QIAGEN Plasmid Mini Handbook for Plasmid Mini Kit", Qiagen GmbH, Hilden, Germany, 1997 I.B.R.) and subsequent agarose gel electrophoresis. The vector constructed consists of the SalI-Ec1136II fragment of pSELF2000 and the PCR amplification product of the panD gene from Corynebacterium glutamicum ATCC13032 and was called pSELF2000P1. A restriction map of the plasmid is shown in FIG. 8.

EXAMPLE 9

Use of the Antibiotic-free Vector System for Production of Pantothenic Acid with Corynebacterium Glutamicum 9.1 Preparation of the Host To produce a Corynebacterium glutamicum strain which is suitable for pantothenate production, the ilvA gene in the chromosome of Corynebacterium glutamicum ATCC13032Δalr91 (Example 6) was first deleted. For this purpose, the plasmid pBM20 (Mockel et al., Molecular Microbiology 13, 833-842 (1994) I.B.R.) was digested with the restriction enzyme BglII (Pharmacia Biotech Europe GmbH, Freiburg, Germany) and then re-ligated with the enzyme T4 DNA ligase (Roche Diagnostics GmbH, Mannheim, Germany). The ligation batch was then transferred to Escherichia coli DH5αMCR by electroporation and selection was carried out on antibiotic medium no. 3 (Oxoid GmbH, Wesel, Germany) supplemented with 100 μg/ml ampicillin. The presence of plasmids in the transformed bacteria cells was demonstrated by an alkaline lysis method ("QIAprep Miniprep Handbook for Purification of Plasmid DNA", Qiagen GmbH, Hilden, Germany, 1997 I.B.R.). Restriction analyses of the plasmid DNA isolated and comparison of the fragment lengths obtained with DNA fragments of known length showed that a deletion approx. 250 by in size was inserted into the ilvA gene on pBM20. The plasmid was called pBM20ΔBglII.

A DNA fragment approx. 1.5 kb in size was excised from the plasmid pBM20ΔBglII with the restriction enzyme EcoRI (Pharmacia Biotech Europe GmbH, Freiburg, Germany) and cloned in the vector pK18mobsacB (Schäfer et al., Gene 145, 69-73 (1994) I.B.R.). The DNA restriction and the DNA ligation were carried out with the enzyme T4 DNA ligase (Roche Diagnostics GmbH, Mannheim, Germany) in accordance with the manufacturer's instructions. The ligation batch was then transferred by electroporation into the bacteria strain Escherichia coli DH5αMCR and selection was carried out on antibiotic medium no. 3 (Oxoid GmbH, Wesel, Germany) supplemented with 25 µg/ml kanamycin and 20 µg/ml X-Gal (Biosolve BV, Valkenswaard, The Netherlands). The presence of plasmids in the transformed bacteria cells was demonstrated by an alkaline lysis method ("QIAprep® Miniprep Handbook for Purification of Plasmid DNA", Qiagen GmbH, Hilden, Germany, 1997 Restriction analyses of the plasmid DNA isolated and comparison of the fragment lengths obtained with DNA fragments of known length showed that the plasmid isolated and plasmid designated pAilvA comprises DNA of the plasmid pK18mobsacB and the DNA fragment from plasmid pBM20ΔBglII approx. 1.5 kb in size.

The deletion construct pAilvA was transferred to *Corynebacterium glutamicum* ATCC13032Δalr91 by electroporation. The plasmid integration was subjected to selection on LB agar supplemented with 0.4 g/l D-alanine and 25 µg/ml kanamycin. Further construction of an ilvA deletion mutant was carried out in accordance with the test instructions of Schafer et al. (Gene 145, 69-73 (1994)) I.B.R. An individual colony of the integrant strain was cultured overnight in 10 ml LB medium supplemented with 0.4 g/l D-alanine and then plated out on LB agar supplemented with 0.4 g/l D-alanine and 100 g/l sucrose. After incubation of the agar plates overnight at 30° C., individual colonies were transferred in parallel to the four test nutrient media LB agar+0.4 g/l D-alanine, LB agar+0.4 g/l D-alanine+25 µg/ml kanamycin, MM1 minimal agar+0.4 g/l D-alanine and MM1 minimal agar+0.4 g/l D-alanine+2 mM L-isoleucine. MM1 minimal medium is composed of the following components:

| | |
|---|---|
| $(NH_4)SO_4$ | 10 g/l |
| Urea | 3 g/l |
| $K_2HPO_4$ | 1 g/l |
| $MgSO_4 \cdot 7H_2O$ | 0.4 g/l |
| $FeSO_4 \cdot 7H_2O$ | 2 mg/l |
| $MnSO_4 \cdot H_2O$ | 2 mg/l |
| NaCl | 50 mg/l |
| Biotin | 50 µg/l |
| Thiamine•HCl | 500 µg/l |
| Glucose monohydrate | 20 g/l |

After a further incubation of the test nutrient media of 48 hours at 30° C., recombinant clones which grow only on LB agar+0.4 g/l D-alanine and minimal agar+0.4 g/l D-alanine+2 mM L-isoleucine were identified. These clones carry a deletion in the ilvA gene.

To demonstrate the deletion designated ΔilvA46 in the chromosome of *Corynebacterium glutamicum* ATCC13032Δalr91, chromosomal DNA was isolated from a clone and employed as template DNA in a PCR reaction. Chromosomal DNA isolated from *Corynebacterium glutamicum* ATCC13032 was employed as control. The PCR primers were derived from the DNA sequence of the ilvA gene (Möckel et al., Journal of Bacteriology 174, 8065-8072 (1992) I.B.R.):

```
ILVA1:   5'-CGCCATTGCTGAGCATTGAG-3' (SEQ ID No. 19)

ILVA2:   5'-CGGTTGTTGCGCTTGAGGTA-3' (SEQ ID No. 20)
```

(ARK Scientific GmbH, Darmstadt Germany). The PCR reaction was carried out with a PCT-100 thermocycler (MJ Research Inc., Watertown, USA). The amplification was carried out with Taq DNA polymerase (Qiagen, Hilden, Germany) in accordance with the manufacturer's instructions in a total reaction volume of 50 µl. The PCR conditions were established as follows:

2 minutes initial running at 94° C., 90 seconds denaturing at 94° C., 45 seconds primer annealing at 57° C. and 90 seconds extension at 72° C. The amplification steps were repeated 35 times and concluded with an extension step of 5 minutes at 72° C. From the PCR reaction, 3 µl were separated in a 0.8% agarose gel with a DNA length standard (DNA Molecular Weight Marker X, Roche Diagnostics GmbH, Mannheim, Germany) and the amplification of a DNA fragment approx. 1.6 kb in size was demonstrated in this way.

The PCR amplification product was then digested with the enzymes BglII and with SpeI and EcoRV in combination (Pharmacia Biotech Europe GmbH, Freiburg, Germany). The restriction batches were separated in 0.8% agarose gel with a DNA length standard (DNA Molecular Weight Marker X, Roche Diagnostics GmbH, Mannheim, Germany) and the absence of a BglII restriction cleavage site and the deletion formation in the ilvA gene were demonstrated in this manner. The resulting strain was called *Corynebacterium glutamicum* ATCC13032Δalr91ΔilvA46.

9.2 Preparation of the Pantothenic Acid Producer

To prepare the pantothenic acid producer, in each case 1 µg of the plasmid DNA isolated from plasmid pSELF2000P1 (Example 8) and from the control plasmids pSELF2000 and pSELF2000X (Example 7) was transferred to *Corynebacterium glutamicum* ATCC13032Δalr91Δilv46 by electroporation. Selection was carried out on LB agar. The selection agar plates were incubated for 20 hours at 30° C. The plasmid transformation which had taken place was demonstrated by an alkaline lysis method ("QIAGEN Plasmid Mini Handbook for Plasmid Mini Kit", Qiagen GmbH, Hilden, Germany, 1997) and subsequent agarose gel electrophoresis. The strains constructed in this manner, ATCC13032Δalr91Δilv46 [pSELF2000], ATCC13032Δalr91Δilv46 [pSELF2000X] and ATCC13032Δalr91Δilv46 [pSELF2000P1] were employed for the production of pantothenate.

9.3 Preparation of Pantothenic Acid

The bacteria strains were initially cultured for 24 hours at 30° C. in 50 ml LB medium, about 15 to 20 generations being passed through. 1 ml of the bacteria culture was then washed twice with CGXII medium (Keilhauer et al., Journal of Bacteriology 175, 5595-5603, (1993) I.B.R.), to which 2 mM isoleucine (Sigma-Aldrich Chemie GmbH, Deisenhofen, Germany) had been added, transferred to 50 ml CGXII medium supplemented with 2 mM L-isoleucine and cultured for 24 hours at 30° C. The number of generations in this culture was approximately 6. 50 ml CGXII medium which comprised 2 mM L-isoleucine were again inoculated with 3 ml of this culture. After further incubation of the batch for 24 hours at 30° C., corresponding to a number of generations of about 4 to 5, 20 ml of the bacteria culture were pelletized by centrifugation for 10 minutes at 1250×g. The culture supernatant was then subjected to sterile filtration with a Millex-GS filter unit (0.22 µm, Millipore S. A., Molsheim, France). The pantothenic acid concentration in the filtered culture supernatants was determined in accordance with the instructions in the Difco-Manual, 10th Edition (Difco Laboratories, Detroit, Mich., USA) I.B.R. The pantothenic acid concentrations obtained after culturing for 24 hours are summarized in Table 3.

TABLE 3

Pantothenic acid concentration in the culture supernatants of various strains of *Corynebacterium glutamicum*

| Strain | Concentration (ng/ml) |
|---|---|
| ATCC13032Δalr91Δilv46[pSELF2000] | 6.4 |
| ATCC13032Δalr91Δilv46[pSELF2000X] | 6.6 |
| ATCC13032Δalr91Δilv46[pSELF2000P1] | 411 |

EXAMPLE 10

Preparation of D-alanine

To obtain the enzyme alanine racemase, cells of the strain *C. glutamicum* ATCC13032Δalr91/pSELF2000 (see Example 8) were cultured in a shaking flask. For this, the strain was cultured in a nutrient medium suitable for the culturing, the cells were harvested and the enzyme activity of the alanine racemase in the cell-free crude extract was then determined.

For this, the strain was first cultured on an agar plate comprising the medium BMCG4 (Table 4). BMCG4 medium is a further development of a medium suitable for culturing *Corynebacterium glutamicum*, such as has been described by Liebl et al. (Applied Microbiology and Biotechnology, 32:205-210 (1989)) I.B.R.

TABLE 4

Composition of BMCG4 Medium

| Substance | Concentration |
|---|---|
| $(NH_4)_2SO_4$ | 7 g/l |
| $Na_2HPO_4$ | 6 g/l |
| $KH_2PO_4$ | 3 g/l |
| $NH_4Cl$ | 1 g/l |
| $MgSO_4 * 7H_2O$ | 0.4 g/l |
| $FeSO_4 * 7H_2O$ | 0.02 g/l |
| $MnSO_4 * H_2O$ | 2.0 mg/l |
| $Na_2B_4O_7 * 10H_2O$ | 176 µg/l |
| $(NH_4)_6Mo_7O_{24} * 4H_2O$ | 80 µg/l |
| $ZnSO2 * 7H_2O$ | 20 µg/l |
| $CuSO4 * 5H_2O$ | 540 µg/l |
| $MnCl2 * 4H_2O$ | 14 µg/l |
| $FeCl3 * 6H_2O$ | 1.74 mg/l |
| $CaCl2 * 2H_2O$ | 7.5 mg/l |
| D-(+)-Biotin | 50 µg/l |
| Thiamin chloride * HCl | 200 µg/l |
| Protocatechuic acid | 30 mg/l |
| Glucose monohydrate | 10 g/l |

To prepare solid nutrient media, agar-agar was added to the BMCG4 medium in a final concentration of 12 g/l.

To obtain biomass or cells of the strain *C. glutamicum* ATCC13032Δalr91/pSELF2000, a BMCG4 liquid culture (10 ml filling volume in a 100 ml shaking flask) was inoculated starting from a BMCG4 agar plate culture. Incubation of the preculture was carried out at 33° C. and 200 rpm (revolutions per minute) for 48 hours. This preculture was then employed in a ratio of 1% (v/v; volume ratio) for inoculation of the main culture, comprising 50 ml BMCG4 medium in a 500 ml shaking flask. This main culture was incubated at 33° C. and 200 rpm for 48 hours. The dry biomass at the end of the culture was approximately 1.15 wt. %.

The cells produced in this manner were then separated off from the culture broth by centrifugation with a laboratory centrifuge of the Biofuge-Stratos type from Heraeus (Dusseldorf, Germany) at 4000 rpm for 20 minutes, while cooling. The culture supernatant was discarded and the cell residue was resuspended in 20 ml of a sodium/potassium phosphate buffer (50 mM, pH 7.3). A dry biomass of 2.88 wt. % was measured in a sample of this cell suspension by means of a HR73 halogen dry balance from Mettler Toledo (Greifenase, Switzerland). The cells were then broken down by means of glass beads (diameter 0.5 mm) in an IMAC disintegrator for 30 minutes, while cooling with ice-water.

The cell fragments of the crude extract obtained in this manner were then separated off by centrifugation in a laboratory centrifuge of the Biofuge-Stratos type from Heraeus (Düsseldorf, Germany) at 4000 rpm for 20 minutes, while cooling. A protein concentration of 1.1 mg/l could then be measured in the clarified cell-free supernatant of the crude extract by means of the Bradford method. Albumin standards from Merck (Darmstadt, Germany) in concentrations of 0.05 g/l, 0.1 g/l and 0.5 g/l were used as the comparison standard for plotting the calibration line. The extinction of the protein samples was determined in a UVIKON933 UV/VIS photometer from KROTON Instruments (Neufahrn, Germany).

For determination of the enzymatic activity of the alanine racemase, 0.5 ml of an L-alanine solution (10.0 g/l dissolved in a 50 mM phosphate buffer, pH 7.3) was added in a reaction bath to 0.5 ml of the cell-free protein crude extract of the strain C- glutamicum ATCC13032Δalr91/pSELF2000 prepared by the process described above. Incubation was carried out at 33° C. over a total of 120 minutes. During this time, samples were taken after 15, 30, 60 and 120 minutes and the concentration of D-alanine formed was determined. The determination of the concentration of D-alanine was carried out by means of isocratic high pressure liquid chromatography (HPLC; pump from Dr. Knauer GmbH, Berlin, Germany; ERC detector 7515A, ERC Germany). Chiral separation of the individual enantiomers was made possible by a Nucleosil-Chiral-1 column (250×4 mm) from Machery & Nagel (Duren, Germany). A 0.5 mM copper sulfate solution was used as the mobile phase at a flow rate of 1.0 ml per minute and a pre-pressure of 80 bar at a column temperature of 60° C.

Under the conditions described above, after 15 minutes 0.15 g/l, after 30 minutes 0.29 g/l, after 60 minutes 0.49 g/l and after 120 minutes 0.93 g/l D-alanine were measured.

The base pair numbers stated are approximate values obtained in the context of reproducibility of measurements. The abbreviations and designations used have the following meaning:

AvrII: Cleavage site for the restriction enzyme AvrII
Ec1136II: Cleavage site for the restriction enzyme Ec1136II
EcoRI: Cleavage site for the restriction enzyme EcoRI
HpaI: Cleavage site for the restriction enzyme HpaI
MunI: Cleavage site for the restriction enzyme MunI
PstI: Cleavage site for the restriction enzyme PstI
SacI: Cleavage site for the restriction enzyme SacI
SacII: Cleavage site for the restriction enzyme SacII
SalI: Cleavage site for the restriction enzyme SalI
ScaI: Cleavage site for the restriction enzyme ScaI
SpeI: Cleavage site for the restriction enzyme SpeI
SphI: Cleavage site for the restriction enzyme SphI
XbaI: Cleavage site for the restriction enzyme XbaI
XhoI: Cleavage site for the restriction enzyme XhoI
alr: Gene for alanine racemase
alr': 5' fragment of the alr gene
'alr: 3' fragment of the alr gene
bp: Base pairs
KanR: Kanamycin resistance gene
lacZ(a)': 5' part of the lacZα gene fragment
'lacZ(a): 3' part of the lacZα gene fragment
oriV: Replication origin
panD: Gene for the pantothenate biosynthesis protein PanD
pACYC184: DNA segment from plasmid pACYC184
RP4mob: Mobilization site from plasmid RP4
sacB: sacB gene
repA: Gene for the replication protein RepA
tetA: Gene for the tetracycline resistance protein
tetR: Gene for the tetracycline repressor protein The following sequences are contained in the sequence protocol:

| SEQ ID No.: | Description: |
|---|---|
| 1 | Nucleotide sequence of the tetA gene in pTET3 |
| 2 | Amino acid sequence of the TetA resistance protein |
| 3 | Nucleotide sequence of the tetR gene in pTET3 |

| SEQ ID No.: | Description: |
|---|---|
| 4 | Nucleotide sequence of the TetR protein |
| 5 | Nucleotide sequence of the primer ALR1-1 |
| 6 | Nucleotide sequence of the primer ALR4-1 |
| 7 | Amino acid sequence of the alr DNA isolated by PCR |
| 8 | Nucleotide sequence of the DNA sequence 1.8 kbp long containing the alr gene |
| 9 | Amino acid sequence of the Alr protein |
| 10 | Nucleotide sequence of the primer RACA |
| 11 | Nucleotide sequence of the primer RACB |
| 12 | Nucleotide sequence of the Δalr91 allele |
| 13 | Nucleotide sequence of the primer ALRD1 |
| 14 | Nucleotide sequence of the primer ALRD2 |
| 15 | Nucleotide sequence of the primer RACF |
| 16 | Nucleotide sequence of the primer RACH |
| 17 | Nucleotide sequence of the primer PAA1 |
| 18 | Nucleotide sequence of the primer PAMOD |
| 19 | Nucleotide sequence of the primer ILVA1 |
| 20 | Nucleotide sequence of the primer ILVA2 |

We claim:

1. A host-vector system comprising a coryneform host bacterium comprising a chromosomal alr gene which is attenuated or eliminated, and a plasmid which replicates in said host and comprises an isolated polynucleotide selected from the group consisting of a) a polynucleotide which encodes a polypeptide comprising SEQ ID NO:9, b) a polynucleotide which encodes a polypeptide which comprises an amino acid sequence which is at least 91% identical to SEQ ID NO:9, c) a polynucleotide which is a complete complement of the polynucleotides of a) or b), and d) a polynucleotide comprising at least 15 successive bases of SEQ ID NO:8.

2. The host-vector system according to claim 1, wherein the number of copies of the plasmid is at least 1 to 1000.

3. *Corynebacterium glutamicum* ATCC13032Δalr91 deposited as DSM14280.

4. A method for preparing L-amino acids or vitamins comprising fermenting the host-vector system according to claim 1.

5. The method according to claim 4, wherein the host-vector system is fermented in a medium or fermentation broth and the coryneform host bacterium produces one or more chemical compound(s) or the corresponding salt(s) thereof.

6. The method according to claim 5, further comprising b) concentrating the chemical compound(s) or the corresponding salt(s) in the medium or fermentation broth or in the cells of the coryneform host bacterium.

7. The method according to claim 6, further comprising c) isolating the chemical compound(s) and/or the corresponding salt(s).

8. The method according to claim 5, wherein fermentation broth contains a biomass and dissolved constituents and the chemical compound(s) and/or corresponding salts isolated in step c) are isolated together with some or all of the biomass and/or the dissolved constituents of the fermentation broth.

9. The method according to claim 5, wherein the fermentation is carried out in the absence of antibiotics in at least one fermentation stage.

10. The host-vector system according to claim 1, wherein the amino acid sequence of b) is at least 99% identical to SEQ ID NO:9.

11. The host-vector system according to claim 1, wherein the polynucleotide is an RNA.

12. The host-vector system according to claim 1, wherein the polynucleotide of d) comprises nucleotides 487 to 1572 of SEQ ID NO:8.

13. The host-vector system according to claim 1, wherein the polynucleotide encodes a polypeptide consisting of SEQ ID NO:9.

* * * * *

SEQUENCE LISTING

```
<160> NUMBER OF SEQ ID NOS: 20

<210> SEQ ID NO 1
<211> LENGTH: 3960
<212> TYPE: DNA
<213> ORGANISM: Corynebacterium glutamicum
<220> FEATURE:
<221> NAME/KEY: CDS
<222> LOCATION: (2124)..(3272)
<223> OTHER INFORMATION:
<221> NAME/KEY: gene
<222> LOCATION: (1447)..(2013)
<223> OTHER INFORMATION:

<400> SEQUENCE: 1
aagcttgagc atgcttggcg gagattggac ggacggaacg atgacggatt tcaagtggcg      60
ccatttccag ggtgatgtga tcctgtgggc ggtgcgctgg tattgtcgct atccgatcag     120
ctatcgcgac cttgaggaaa tgctggcgga acgcggcatt tcggtcgacc atacgacgat     180
ctatcgctgg gtccagtgct acgccccgga gatggagaag cggctgcgct ggttctggcg     240
gcgtggcttt gatccgagct ggcgcctgga tgaaacctac gtcaaggtgc ggggcaagtg     300
gacctacctg taccgggcag tcgacaagcg gggcgacacg atcgatttct acctgtcgcc     360
gacccgcagc gccaaggcag cgaagcggtt cctgggcaag gccctgcgag gcctgaagca     420
ctgggaaaag cctgccacgc tcaataccga caaagcgccc agctatggtg cagcgatcac     480
cgaattgaag cgcgaaggaa agctggaccg ggagacggcc caccggcagg tgaagtatct     540
caataacgtg atcgaggccg atcacggaaa gctcaagata ctgatcaagc cggtgcgcgg     600
tttcaaatcg atccccacgg cctatgccac gatcaaggga ttcgaagtca tgcgagccct     660
gcgcaaagga caggctcgcc cctggtgcct gcagcccggc atcaggggcg aggtgcgcct     720
tgtggagaga gctttttggca ttgggccctc ggcgctgacg gaggccatgg gcatgctcaa     780
ccaccatttc gcagcagccg cctgatcggc gcagagcgac agcctacctc tgactgccgc     840
caatctttgc aacagagcct ttgcgtcaat gcagggagat agcgaagagc gcgcttcaac     900
ggagatgctc gaatgggtcc acgacggatt ggagtccgtg gtcgcggcag acgtagatga     960
ttcgcacgcc gtacccgtcg gcgccgctcg gctcggggtc gcattctgcg cggcagacgt    1020
tacagagccg gtgctcgttg ctcccccaga ccgtgacctc gatatcgtcg gggatctcca    1080
ttccgtcgaa ctccatatgc ggaggttagc tgtcgcggat tgagtcgtgt caagatgcgg    1140
caccgatgct aaaccgccgt tacctatggt catcgcgccg gtcgcgcact cgacgcttag    1200
ttcttgaggt actcgaggac ggcgatgacg cgcttgttcc ctgtgcgctc gttaaggtcg    1260
agcatggtga agatgctgct gatgtgccgt tccgcgatcg cgacgcgaca tgcacacggt    1320
```

```
ccctgatttg ctcgtttgtg agccccgtag ccatgagcga atcgtcagta tcgcggagga   1380
ggtgctgcgg gagcgggaaa ggattgacct tactgacgca gagacccaaa gtgcgagcat   1440
ccctcatcgc tttgatgcca gcccttcaac cattgcaact aacccgaact cgaaatctag   1500
gtcttgatcg acaggctcac atccgttgtc gagcgctgtt tgttcttcta gtacgaaacc   1560
gaccgtatag cggctgatag ccatgagagc tcggaccgca gagccctcag cgaatccttc   1620
ggacacgaga aactcgatct gactttcggg ggcatccgag cccgctggca tctggtcact   1680
cttttgacgg tgaaactctg cgtgcagccg tgctccatcc cggactgcca aagcgctgt    1740 ccggaagctc cgcgcgttgc gcaggagaaa gtcgtcccag cgctcccctg actctgggag   1800
tgaggcgtgg tgttcgcgat caagcacatc agctgcgagc gatccgagca ggtgggcctt   1860
tgtccgaaag tgccagtaga gcgctggctg ctgcacccgc agatgcgcag ccagcgcccg   1920
tgtggtgaaa ccgtcgatcc ccgtgttatt gagcacatgc ctcgcaccgc gcaagactgc   1980
tgcacgatcg agtcgcgctt gtttctgagc catgcttgca ctttatcatc gataacttta   2040
tcgttgataa ggtgtcatct ctcacttccg ctcgtggctc gttggccacg gtcctcatca   2100
cggctagcct cgacgccgcc ggc atg ggc ctg gtg atg ccg att ctt ccc gca   2153
                         Met Gly Leu Val Met Pro Ile Leu Pro Ala
                           1               5                  10 ctg cta cac gag gca ggg gtc acc gct gat gcg gtt ccg ctg aac gtc   2201
Leu Leu His Glu Ala Gly Val Thr Ala Asp Ala Val Pro Leu Asn Val
             15                  20                  25 gga gtg ctg atc gcg ctc tac gcg gta atg cag ttc atc ttt gcc ccc   2249
Gly Val Leu Ile Ala Leu Tyr Ala Val Met Gln Phe Ile Phe Ala Pro
         30                  35                  40 gta ctg gga acg ctg tcg gac cga ttc ggc cgc cgc cgg gtg ctg ctt   2297
Val Leu Gly Thr Leu Ser Asp Arg Phe Gly Arg Arg Arg Val Leu Leu
     45                  50                  55 gtt tcc ctg gcc ggt gcg acc gtc gac tat ctc gtg ctc gcc acg acg   2345
Val Ser Leu Ala Gly Ala Thr Val Asp Tyr Leu Val Leu Ala Thr Thr
 60                  65                  70 tcc gct ctg tcg gtg ttc tat atc gcc cgc gca gtg gct ggg ata acc   2393
Ser Ala Leu Ser Val Phe Tyr Ile Ala Arg Ala Val Ala Gly Ile Thr
 75                  80                  85                  90 gga gcg acc aat gcg gtc acc gcc acc gtg atc gcc gac atc acg cca   2441
Gly Ala Thr Asn Ala Val Thr Ala Thr Val Ile Ala Asp Ile Thr Pro
             95                 100                 105 ccc cac cag cgc gcc aag cgt ttc ggt tta ctc agt gcc tgc tat ggc   2489
Pro His Gln Arg Ala Lys Arg Phe Gly Leu Leu Ser Ala Cys Tyr Gly
         110                 115                 120 ggc gga atg atc gcg ggg cca gcc atg ggt gga ctg ttc ggt gcc atc   2537
Gly Gly Met Ile Ala Gly Pro Ala Met Gly Gly Leu Phe Gly Ala Ile
     125                 130                 135 tcg cca cat ctg ccg ttt ttg ctc gct gct ctt ctc tca gcg agc aat   2585
Ser Pro His Leu Pro Phe Leu Leu Ala Ala Leu Leu Ser Ala Ser Asn
 140                 145                 150 ctg gca ctc acc ttt atc ctg tta cgc gag acc cgt cct gat tcc cct   2633
Leu Ala Leu Thr Phe Ile Leu Leu Arg Glu Thr Arg Pro Asp Ser Pro
155                 160                 165                 170 gcg cgc tct gcg tcg ctc gct cag cat cgt ggt cgc ccc ggc ctc agc   2681
Ala Arg Ser Ala Ser Leu Ala Gln His Arg Gly Arg Pro Gly Leu Ser
             175                 180                 185 gcg gtg cct ggg att acc ttc cta tta atc gca ttc ggc ctt gtt caa   2729
Ala Val Pro Gly Ile Thr Phe Leu Leu Ile Ala Phe Gly Leu Val Gln
         190                 195                 200
```

```
ttc att ggg cag gct cca ggt gcg acc tgg gtg ctg ttt act gaa cac        2777
Phe Ile Gly Gln Ala Pro Gly Ala Thr Trp Val Leu Phe Thr Glu His
        205                 210                 215 cgc ctc gac tgg agt ccc gtc gaa gtt gga atc tcc ctg tcc gtt ttc        2825
Arg Leu Asp Trp Ser Pro Val Glu Val Gly Ile Ser Leu Ser Val Phe
    220                 225                 230 ggg atc gta cag gtt ctc gtg cag gcc ctc ctt act ggc cgc atc gtg        2873
Gly Ile Val Gln Val Leu Val Gln Ala Leu Leu Thr Gly Arg Ile Val
235                 240                 245                 250 gag tgg atc ggt gag gca aaa aca gtc atc atc ggg tgt att acc gac        2921
Glu Trp Ile Gly Glu Ala Lys Thr Val Ile Ile Gly Cys Ile Thr Asp
                255                 260                 265 gcc ttg ggt ctc gta ggc ctg gcg att gtc act gac gca ttt tcc atg        2969
Ala Leu Gly Leu Val Gly Leu Ala Ile Val Thr Asp Ala Phe Ser Met
        270                 275                 280 gca cct atc ttg gcg gca ctg ggg atc ggt ggc atc ggc ctc ccc gct        3017
Ala Pro Ile Leu Ala Ala Leu Gly Ile Gly Gly Ile Gly Leu Pro Ala
    285                 290                 295 ctg caa acc ctt ctc tcc cag cgc gtc gat gaa cag cac caa ggg cgc        3065
Leu Gln Thr Leu Leu Ser Gln Arg Val Asp Glu Gln His Gln Gly Arg
300                 305                 310 ctc cag ggt gtg ctc gcc agc atc aac agc gtc aca tcg atc ttc gga        3113
Leu Gln Gly Val Leu Ala Ser Ile Asn Ser Val Thr Ser Ile Phe Gly
315                 320                 325                 330 ccg gtc gct ttc aca acg atc ttc gcg ctc act tac atc aac gcc gac        3161
Pro Val Ala Phe Thr Thr Ile Phe Ala Leu Thr Tyr Ile Asn Ala Asp
                335                 340                 345 ggc ttc ctc tgg ctc tgc gcc gca gca ctc tac gtg ccc tgc gtg att        3209
Gly Phe Leu Trp Leu Cys Ala Ala Ala Leu Tyr Val Pro Cys Val Ile
        350                 355                 360 ctc atc atg cgt ggt aca gca gcg tcc ccg aag ttc ggc tct tgg gcg        3257
Leu Ile Met Arg Gly Thr Ala Ala Ser Pro Lys Phe Gly Ser Trp Ala
    365                 370                 375 agc ggc gac tcg atg tgagttgtga cacgtgagca ggagcaacac ggcggcgaca       3312
Ser Gly Asp Ser Met
    380 ctgcttcgcc atggccgact agcgagacgg cgccaccggg aaactcggca tcatctacca     3372 aggacaggtc agctgggagc ctgatagacc catcgaaatg tgcgtgccga tcgcggagaa     3432 gggccgggcg catcggatcg agccatagca ccatgagtct tcacggaagt gcgtcgacgg     3492 agacttggtt gtgaaccggg ccaagggaga gctggaggcc ctctccgagt ggcttgccga     3552 tgacatgagc tggacgctca tcgagaaatc cacacacagc ggccccagtg cagcccgaga     3612 ggtgcgcccg ccgttctccc gagcgggtgg aggtcatttc tgtcgtcacc cacggacgac     3672 gcgcttcctg cgacggctac ctcgaggctg aggaatgcg cgtccgtttc agccatgcgt      3732 tccgcttcgt cagcaccccc aagacctcga tgatcgcaga actgcgacgc tactgcatcg     3792 agacgcaggt tgactgaggc ctgtgcggac agcacgaacg acccttgagc ccgtaatctg     3852 ggaaccgcag aaactacccg atcgaaacgc aactactttg ccgaccctac ggggttggct     3912 cgcggtcgtc gtccttggcc gggctctgtt gcaaaaatcg tgaagctt                  3960
```

<210> SEQ ID NO 2
<211> LENGTH: 383
<212> TYPE: PRT
<213> ORGANISM: Corynebacterium glutamicum

<400> SEQUENCE: 2

```
Met Gly Leu Val Met Pro Ile Leu Pro Ala Leu Leu His Glu Ala Gly
1               5                   10                  15

Val Thr Ala Asp Ala Val Pro Leu Asn Val Gly Val Leu Ile Ala Leu
            20                  25                  30

Tyr Ala Val Met Gln Phe Ile Phe Ala Pro Val Leu Gly Thr Leu Ser
        35                  40                  45

Asp Arg Phe Gly Arg Arg Val Leu Leu Val Ser Leu Ala Gly Ala
    50                  55                  60

Thr Val Asp Tyr Leu Val Leu Ala Thr Thr Ser Ala Leu Ser Val Phe
65                  70                  75                  80

Tyr Ile Ala Arg Ala Val Ala Gly Ile Thr Gly Ala Thr Asn Ala Val
                85                  90                  95

Thr Ala Thr Val Ile Ala Asp Ile Thr Pro Pro His Gln Arg Ala Lys
            100                 105                 110

Arg Phe Gly Leu Leu Ser Ala Cys Tyr Gly Gly Met Ile Ala Gly
        115                 120                 125

Pro Ala Met Gly Gly Leu Phe Gly Ala Ile Ser Pro His Leu Pro Phe
    130                 135                 140

Leu Leu Ala Ala Leu Leu Ser Ala Ser Asn Leu Ala Leu Thr Phe Ile
145                 150                 155                 160

Leu Leu Arg Glu Thr Arg Pro Asp Ser Pro Ala Arg Ser Ala Ser Leu
                165                 170                 175

Ala Gln His Arg Gly Arg Pro Gly Leu Ser Ala Val Pro Gly Ile Thr
            180                 185                 190

Phe Leu Leu Ile Ala Phe Gly Leu Val Gln Phe Ile Gly Gln Ala Pro
        195                 200                 205

Gly Ala Thr Trp Val Leu Phe Thr Glu His Arg Leu Asp Trp Ser Pro
    210                 215                 220

Val Glu Val Gly Ile Ser Leu Ser Val Phe Gly Ile Val Gln Val Leu
225                 230                 235                 240

Val Gln Ala Leu Leu Thr Gly Arg Ile Val Glu Trp Ile Gly Glu Ala
                245                 250                 255

Lys Thr Val Ile Ile Gly Cys Ile Thr Asp Ala Leu Gly Leu Val Gly
            260                 265                 270

Leu Ala Ile Val Thr Asp Ala Phe Ser Met Ala Pro Ile Leu Ala Ala
        275                 280                 285

Leu Gly Ile Gly Ile Gly Leu Pro Ala Leu Gln Thr Leu Leu Ser
    290                 295                 300

Gln Arg Val Asp Glu Gln His Gln Gly Arg Leu Gln Gly Val Leu Ala
305                 310                 315                 320

Ser Ile Asn Ser Val Thr Ser Ile Phe Gly Pro Val Ala Phe Thr Thr
                325                 330                 335

Ile Phe Ala Leu Thr Tyr Ile Asn Ala Asp Gly Phe Leu Trp Leu Cys
            340                 345                 350

Ala Ala Ala Leu Tyr Val Pro Cys Val Ile Leu Ile Met Arg Gly Thr
        355                 360                 365

Ala Ala Ser Pro Lys Phe Gly Ser Trp Ala Ser Gly Asp Ser Met
    370                 375                 380
```

<210> SEQ ID NO 3
<211> LENGTH: 570
<212> TYPE: DNA
<213> ORGANISM: Corynebacterium glutamicum

```
<220> FEATURE:
<221> NAME/KEY: CDS
<222> LOCATION: (1)..(567)
<223> OTHER INFORMATION:

<400> SEQUENCE: 3 atg gct cag aaa caa gcg cga ctc gat cgt gca gca gtc ttg cgc ggt        48
Met Ala Gln Lys Gln Ala Arg Leu Asp Arg Ala Ala Val Leu Arg Gly
1               5                   10                  15 gcg agg cat gtg ctc aat aac acg ggg atc gac ggt ttc acc aca cgg        96
Ala Arg His Val Leu Asn Asn Thr Gly Ile Asp Gly Phe Thr Thr Arg
            20                  25                  30 gcg ctg gct gcg cat ctg cgg gtg cag cag cca gcg ctc tac tgg cac       144
Ala Leu Ala Ala His Leu Arg Val Gln Gln Pro Ala Leu Tyr Trp His
        35                  40                  45 ttt cgg aca aag gcc cac ctg ctc gga tcg ctc gca gct gat gtg ctt       192
Phe Arg Thr Lys Ala His Leu Leu Gly Ser Leu Ala Ala Asp Val Leu
50                  55                  60 gat cgc gaa cac cac gcc tca ctc cca gag tca ggg gag cgc tgg gac       240
Asp Arg Glu His His Ala Ser Leu Pro Glu Ser Gly Glu Arg Trp Asp
65                  70                  75                  80 gac ttt ctc ctg cgc aac gcg cgg agc ttc cgg aca gcg ctt ctg gca       288
Asp Phe Leu Leu Arg Asn Ala Arg Ser Phe Arg Thr Ala Leu Leu Ala
                85                  90                  95 gtc cgg gat gga gca cgg ctg cac gca gag ttt cac cgt caa aag agt       336
Val Arg Asp Gly Ala Arg Leu His Ala Glu Phe His Arg Gln Lys Ser
            100                 105                 110 gac cag atg cca gcg ggc tcg gat gcc ccc gaa agt cag atc gag ttt       384
Asp Gln Met Pro Ala Gly Ser Asp Ala Pro Glu Ser Gln Ile Glu Phe
        115                 120                 125 ctc gtg tcc gaa gga ttc gct gag ggc tct gcg gtc cga gct ctc atg       432
Leu Val Ser Glu Gly Phe Ala Glu Gly Ser Ala Val Arg Ala Leu Met
130                 135                 140 gct atc agc cgc tat acg gtc ggt ttc gta cta gaa gaa caa aca gcg       480
Ala Ile Ser Arg Tyr Thr Val Gly Phe Val Leu Glu Glu Gln Thr Ala
145                 150                 155                 160 ctc gac aac gga tgt gag cct gtc gat caa gac cta gat ttc gag ttc       528
Leu Asp Asn Gly Cys Glu Pro Val Asp Gln Asp Leu Asp Phe Glu Phe
                165                 170                 175 ggg tta gtt gca atg gtt gaa ggg ctg gca tca aag cga tga               570
Gly Leu Val Ala Met Val Glu Gly Leu Ala Ser Lys Arg
            180                 185

<210> SEQ ID NO 4
<211> LENGTH: 189
<212> TYPE: PRT
<213> ORGANISM: Corynebacterium glutamicum

<400> SEQUENCE: 4

Met Ala Gln Lys Gln Ala Arg Leu Asp Arg Ala Ala Val Leu Arg Gly
1               5                   10                  15

Ala Arg His Val Leu Asn Asn Thr Gly Ile Asp Gly Phe Thr Thr Arg
            20                  25                  30

Ala Leu Ala Ala His Leu Arg Val Gln Gln Pro Ala Leu Tyr Trp His
        35                  40                  45

Phe Arg Thr Lys Ala His Leu Leu Gly Ser Leu Ala Ala Asp Val Leu
50                  55                  60

Asp Arg Glu His His Ala Ser Leu Pro Glu Ser Gly Glu Arg Trp Asp
65                  70                  75                  80

Asp Phe Leu Leu Arg Asn Ala Arg Ser Phe Arg Thr Ala Leu Leu Ala
                85                  90                  95
```

```
Val Arg Asp Gly Ala Arg Leu His Ala Glu Phe His Arg Gln Lys Ser
        100                 105                 110
Asp Gln Met Pro Ala Gly Ser Asp Ala Pro Glu Ser Gln Ile Glu Phe
        115                 120                 125
Leu Val Ser Glu Gly Phe Ala Glu Gly Ser Ala Val Arg Ala Leu Met
        130                 135                 140
Ala Ile Ser Arg Tyr Thr Val Gly Phe Val Leu Glu Glu Gln Thr Ala
145                 150                 155                 160
Leu Asp Asn Gly Cys Glu Pro Val Asp Gln Asp Leu Asp Phe Glu Phe
                165                 170                 175
Gly Leu Val Ala Met Val Glu Gly Leu Ala Ser Lys Arg
        180                 185

<210> SEQ ID NO 5
<211> LENGTH: 20
<212> TYPE: DNA
<213> ORGANISM: Corynebacterium glutamicum

<400> SEQUENCE: 5
ctgatggcgg tggtsaaggc                                                 20

<210> SEQ ID NO 6
<211> LENGTH: 22
<212> TYPE: DNA
<213> ORGANISM: Corynebacterium glutamicum

<400> SEQUENCE: 6
cgaactgatc catgcataag cg                                              22

<210> SEQ ID NO 7
<211> LENGTH: 838
<212> TYPE: DNA
<213> ORGANISM: Corynebacterium glutamicum

<400> SEQUENCE: 7
ctgatggcgg tggtcaaggc gaatgcatat aaccatggcg tagagaaggt cgctccggtt     60
attgctgctc atggtgcgga tgcgtttggt gtggcaactc ttgcggaggc tatgcagttg    120
cgtgatatcg gcatcagcca agaggttttg tgttggattt ggacaccgga gcaggatttc    180
cgcgccgcca ttgatcgcaa tattgatttg gctgttattt ctcccgcgca tgccaaagcc    240
ttgatcgaaa ctgatgcgga gcatattcgg gtgtccatca agattgattc tgggttgcat    300
cgttcgggtg tggatgagca ggagtgggag ggcgtgttca gcgcgttggc tgctgccccg    360
cacattgagg tcacgggcat gttcacgcac ttggcgtgcg cggatgagcc agagaatccg    420
gaaactgatc gccaaattat tgcttttcga cgcgcccttg cgctcgcccg caagcacggg    480
cttgagtgcc cggtcaacca cgtatgcaac tcacctgcat tcttgactcg atctgattta    540
cacatggaga tggtccgacc gggtttggcc ttttatgggt tggaacccgt ggcgggactg    600
gagcatggtt tgaagccggc gatgacgtgg gaggcgaagg tgagcgtcgt aaagcaaatt    660
gaagctggac aaggcacttc ctatggcctg acctggcgcg ctgaggatcg cggctttgtg    720
gctgtggtgc ctgcgggcta tgccgatggc atgccgcggc atgcccaggg gaaattctcc    780
gtcacgattg atggcctgga ctatccgcag gttgggcgct tatgcatgga tcagttcg     838

<210> SEQ ID NO 8
<211> LENGTH: 1843
<212> TYPE: DNA
<213> ORGANISM: Corynebacterium glutamicum
```

```
<220> FEATURE:
<221> NAME/KEY: CDS
<222> LOCATION: (487)..(1572)
<223> OTHER INFORMATION:

<400> SEQUENCE: 8
agtactgcag cccagcacc catgccgtgg cctactacac cgaggcaggc tgggttgacg      60
gtgacgtttc cggagccgag ttttacgccg ccgagaatct gaatggagga ttcgaggtca    120
gaggcgaaac ctttgtggtc tggcatgaag ccatttttcgg tgtctggggc ggcaacagcg   180 atgcccagg acgcgaggtg tcgcaaagtt tggtggtagt acttgatgga tttcatccag     240
tcgtggccga agctacacc tgggatgccg tcgccttctg ctggggtgta gattttgccc     300
gggatgccgg cgtagttcat atcgcctacc agcacgcggt gcggtccgcg cttggacagt    360
ttggacaggt gtttgttcag attctcagcc acgtgtttaa ggatagttga aagcgtgggg    420
caatactggc actaaccccg gcaccaatcg tatttctgtc cgcggttggt ggcacaatag    480 ttcaac atg aac ttg ctg acc acc aaa att gac ctg gat gcc atc gcc      528
       Met Asn Leu Leu Thr Thr Lys Ile Asp Leu Asp Ala Ile Ala
         1               5                  10 cat aac acg agg gtg ctt aaa caa atg gcg ggt ccg gcg aag ctg atg      576
His Asn Thr Arg Val Leu Lys Gln Met Ala Gly Pro Ala Lys Leu Met
 15                  20                  25                  30 gcg gtg gtg aag gcg aat gca tat aac cat ggc gta gag aag gtc gct      624
Ala Val Val Lys Ala Asn Ala Tyr Asn His Gly Val Glu Lys Val Ala
                 35                  40                  45 ccg gtt att gct gct cat ggt gcg gat gcg ttt ggt gtg gca act ctt      672
Pro Val Ile Ala Ala His Gly Ala Asp Ala Phe Gly Val Ala Thr Leu
             50                  55                  60 gcg gag gct atg cag ttg cgt gat atc ggc atc agc caa gag gtt ttg      720
Ala Glu Ala Met Gln Leu Arg Asp Ile Gly Ile Ser Gln Glu Val Leu
 65                  70                  75 tgt tgg att tgg aca ccg gag cag gat ttc cgc gcc gcc att gat cgc      768
Cys Trp Ile Trp Thr Pro Glu Gln Asp Phe Arg Ala Ala Ile Asp Arg
         80                  85                  90 aat att gat ttg gct gtt att tct ccc gcg cat gcc aaa gcc ttg atc      816
Asn Ile Asp Leu Ala Val Ile Ser Pro Ala His Ala Lys Ala Leu Ile
 95                 100                 105                 110 gaa act gat gcg gag cat att cgg gtg tcc atc aag att gat tct ggg      864
Glu Thr Asp Ala Glu His Ile Arg Val Ser Ile Lys Ile Asp Ser Gly
                115                 120                 125 ttg cat cgt tcg ggt gtg gat gag cag gag tgg gag ggc gtg ttc agc      912
Leu His Arg Ser Gly Val Asp Glu Gln Glu Trp Glu Gly Val Phe Ser
            130                 135                 140 gcg ttg gct gct gcc ccg cac att gag gtc acg ggc atg ttc acg cac      960
Ala Leu Ala Ala Ala Pro His Ile Glu Val Thr Gly Met Phe Thr His
145                 150                 155 ttg gcg tgc gcg gat gag cca gag aat ccg gaa act gat cgc caa att     1008
Leu Ala Cys Ala Asp Glu Pro Glu Asn Pro Glu Thr Asp Arg Gln Ile
        160                 165                 170 att gct ttt cga cgc gcc ctt gcg ctc gcc cgc aag cac ggg ctt gag     1056
Ile Ala Phe Arg Arg Ala Leu Ala Leu Ala Arg Lys His Gly Leu Glu
175                 180                 185                 190 tgc ccg gtc aac cac gta tgc aac tca cct gca ttc ttg act cga tct     1104
Cys Pro Val Asn His Val Cys Asn Ser Pro Ala Phe Leu Thr Arg Ser
                195                 200                 205 gat tta cac atg gag atg gtc cga ccg ggt ttg gcc ttt tat ggg ttg     1152
Asp Leu His Met Glu Met Val Arg Pro Gly Leu Ala Phe Tyr Gly Leu
            210                 215                 220
```

```
gaa ccc gtg gcg gga ctg gag cat ggt ttg aag ccg gcg atg acg tgg    1200
Glu Pro Val Ala Gly Leu Glu His Gly Leu Lys Pro Ala Met Thr Trp
        225                 230                 235 gag gcg aag gtg agc gtc gta aag caa att gaa gct gga caa ggc act    1248
Glu Ala Lys Val Ser Val Val Lys Gln Ile Glu Ala Gly Gln Gly Thr
240                 245                 250 tcc tat ggc ctg acc tgg cgc gct gag gat cgc ggc ttt gtg gct gtg    1296
Ser Tyr Gly Leu Thr Trp Arg Ala Glu Asp Arg Gly Phe Val Ala Val
255                 260                 265                 270 gtg cct gcg ggc tat gcc gat ggc atg ccg cgg cat gcc cag ggg aaa    1344
Val Pro Ala Gly Tyr Ala Asp Gly Met Pro Arg His Ala Gln Gly Lys
            275                 280                 285 ttc tcc gtc acg att gat ggc ctg gac tat ccg cag gtt ggg cgc gta    1392
Phe Ser Val Thr Ile Asp Gly Leu Asp Tyr Pro Gln Val Gly Arg Val
        290                 295                 300 tgc atg gat cag ttc gtt att tct ttg ggc gac aat cca cac ggc gtg    1440
Cys Met Asp Gln Phe Val Ile Ser Leu Gly Asp Asn Pro His Gly Val
305                 310                 315 gaa gct ggg gcg aag gcc gtg ata ttc ggt gag aat ggg cat gac gca    1488
Glu Ala Gly Ala Lys Ala Val Ile Phe Gly Glu Asn Gly His Asp Ala
320                 325                 330 act gat ttt gcg gag cgt tta gac acc att aac tat gag gta gtg tgc    1536
Thr Asp Phe Ala Glu Arg Leu Asp Thr Ile Asn Tyr Glu Val Val Cys
335                 340                 345                 350 cga cca acc ggc cga act gtc cgc gca tat gtt taa gtgaatacgt         1582
Arg Pro Thr Gly Arg Thr Val Arg Ala Tyr Val
            355                 360 ttaaggagca gcaatgaaat ctgagtttcc ggtatccggc acgaggcgtt ttgagcatgc  1642
cgcagatacc caaaattttg gggaagaatt aggcaggcat ctagaagctg gcgatgtggt  1702
gattttggac ggcccgctgg gtgctggaaa aaccacattt actcaaggta tcgctcgtgg  1762
attgcaggtg aagggcgggt gacatcgcc gacgtttgtg atcgcgaggg aacaccgctc   1822
ggaaatcggt gggccagatc t                                            1843

<210> SEQ ID NO 9
<211> LENGTH: 361
<212> TYPE: PRT
<213> ORGANISM: Corynebacterium glutamicum

<400> SEQUENCE: 9

Met Asn Leu Leu Thr Thr Lys Ile Asp Leu Asp Ala Ile Ala His Asn
1               5                   10                  15

Thr Arg Val Leu Lys Gln Met Ala Gly Pro Ala Lys Leu Met Ala Val
            20                  25                  30

Val Lys Ala Asn Ala Tyr Asn His Gly Val Glu Lys Val Ala Pro Val
        35                  40                  45

Ile Ala Ala His Gly Ala Asp Ala Phe Gly Val Ala Thr Leu Ala Glu
    50                  55                  60

Ala Met Gln Leu Arg Asp Ile Gly Ile Ser Gln Glu Val Leu Cys Trp
65                  70                  75                  80

Ile Trp Thr Pro Glu Gln Asp Phe Arg Ala Ala Ile Asp Arg Asn Ile
                85                  90                  95

Asp Leu Ala Val Ile Ser Pro Ala His Ala Lys Ala Leu Ile Glu Thr
            100                 105                 110

Asp Ala Glu His Ile Arg Val Ser Ile Lys Ile Asp Ser Gly Leu His
        115                 120                 125

Arg Ser Gly Val Asp Glu Gln Glu Trp Glu Gly Val Phe Ser Ala Leu
    130                 135                 140
```

```
Ala Ala Ala Pro His Ile Glu Val Thr Gly Met Phe Thr His Leu Ala
145                 150                 155                 160

Cys Ala Asp Glu Pro Glu Asn Pro Glu Thr Asp Arg Gln Ile Ile Ala
            165                 170                 175

Phe Arg Arg Ala Leu Ala Leu Ala Arg Lys His Gly Leu Glu Cys Pro
        180                 185                 190

Val Asn His Val Cys Asn Ser Pro Ala Phe Leu Thr Arg Ser Asp Leu
    195                 200                 205

His Met Glu Met Val Arg Pro Gly Leu Ala Phe Tyr Gly Leu Glu Pro
210                 215                 220

Val Ala Gly Leu Glu His Gly Leu Lys Pro Ala Met Thr Trp Glu Ala
225                 230                 235                 240

Lys Val Ser Val Val Lys Gln Ile Glu Ala Gly Gln Gly Thr Ser Tyr
                245                 250                 255

Gly Leu Thr Trp Arg Ala Glu Asp Arg Gly Phe Val Ala Val Val Pro
            260                 265                 270

Ala Gly Tyr Ala Asp Gly Met Pro Arg His Ala Gln Gly Lys Phe Ser
        275                 280                 285

Val Thr Ile Asp Gly Leu Asp Tyr Pro Gln Val Gly Arg Val Cys Met
    290                 295                 300

Asp Gln Phe Val Ile Ser Leu Gly Asp Asn Pro His Gly Val Glu Ala
305                 310                 315                 320

Gly Ala Lys Ala Val Ile Phe Gly Asn Gly His Asp Ala Thr Asp
                325                 330                 335

Phe Ala Glu Arg Leu Asp Thr Ile Asn Tyr Glu Val Val Cys Arg Pro
            340                 345                 350

Thr Gly Arg Thr Val Arg Ala Tyr Val
        355                 360

<210> SEQ ID NO 10
<211> LENGTH: 20
<212> TYPE: DNA
<213> ORGANISM: Corynebacterium glutamicum

<400> SEQUENCE: 10
ggtatctgcg gcatgctcaa                                                 20

<210> SEQ ID NO 11
<211> LENGTH: 20
<212> TYPE: DNA
<213> ORGANISM: Corynebacterium glutamicum

<400> SEQUENCE: 11
tcatatcgcc taccagcacg                                                 20

<210> SEQ ID NO 12
<211> LENGTH: 1261
<212> TYPE: DNA
<213> ORGANISM: Corynebacterium glutamicum
<220> FEATURE:
<221> NAME/KEY: allele
<222> LOCATION: (1)..(1261)
<223> OTHER INFORMATION: delta alr91 allele
<221> NAME/KEY: misc_feature
<222> LOCATION: (1)..(170)
<223> OTHER INFORMATION: upstream region
<221> NAME/KEY: misc_feature
<222> LOCATION: (171)..(380)
<223> OTHER INFORMATION: N-terminal remaining sequence of the alr gene
<221> NAME/KEY: misc_feature
<222> LOCATION: (381)..(1178)
<223> OTHER INFORMATION: C-terminal remaining sequence of the alr gene
```

<221> NAME/KEY: misc_feature
<222> LOCATION: (1179)..(1181)
<223> OTHER INFORMATION: stop codon
<221> NAME/KEY: misc_feature
<222> LOCATION: (1182)..(1261)
<223> OTHER INFORMATION: downstream region

<400> SEQUENCE: 12

```
tcatatcgcc taccagcacg cggtgcggtc cgcgcttgga cagtttggac aggtgtttgt      60
tcagattctc agccacgtgt ttaaggatag ttgaaagcgt ggggcaatac tggcactaac     120
cccggcacca atcgtatttc tgtccgcggt tggtggcaca atagttcaac atgaacttgc     180
tgaccaccaa aattgacctg gatgccatcg cccataacac gagggtgctt aaacaaatgg     240
cgggtccggc gaagctgatg gcggtggtga aggcgaatgc atataaccat ggcgtagaga     300
aggtcgctcc ggttattgct gctcatggtg cggatgcgtt tggtgtggca actcttgcgg     360
aggctatgca gttgcgtgat attgatttgg ctgttatttc tcccgcgcat gccaaagcct     420
tgatcgaaac tgatgcggag catattcggg tgtccatcaa gattgattct gggttgcatc     480
gttcgggtgt ggatgagcag gagtgggagg gcgtgttcag cgcgttggct gctgccccgc     540
acattgaggt cacgggcatg ttcacgcact tggcgtgcgc ggatgagcca gagaatccgg     600
aaactgatcg ccaaattatt gcttttcgac gcgcccttgc gctcgcccgc aagcacgggc     660
ttgagtgccc ggtcaaccac gtatgcaact cacctgcatt cttgactcga tctgatttac     720
acatggagat ggtccgaccg ggtttggcct tttatgggtt ggaacccgtg gcgggactgg     780
agcatggttt gaagccggcg atgacgtggg aggcgaaggt gagcgtcgta aagcaaattg     840
aagctggaca aggcacttcc tatggcctga cctggcgcgc tgaggatcgc ggctttgtgg     900
ctgtggtgcc tgcgggctat gccgatggca tgccgcggca tgcccagggg aaattctccg     960
tcacgattga tggcctggac tatccgcagg ttgggcgcgt atgcatggat cagttcgtta    1020
tttctttggg cgacaatcca cacggcgtgg aagctgggc gaaggccgtg atattcggtg    1080
agaatgggca tgacgcaact gattttgcgg agcgtttaga caccattaac tatgaggtag    1140
tgtgccgacc aaccggccga actgtccgcg catatgttta agtgaatacg tttaaggagc    1200
agcaatgaaa tctgagtttc cggtatccgg cacgaggcgt tttgagcatg ccgcagatac    1260
c                                                                    1261
```

<210> SEQ ID NO 13
<211> LENGTH: 20
<212> TYPE: DNA
<213> ORGANISM: Corynebacterium glutamicum

<400> SEQUENCE: 13

```
ggttggtggc acaatagttc                                                  20
```

<210> SEQ ID NO 14
<211> LENGTH: 20
<212> TYPE: DNA
<213> ORGANISM: Corynebacterium glutamicum

<400> SEQUENCE: 14

```
ggtgagttgc atacgtggtt                                                  20
```

<210> SEQ ID NO 15
<211> LENGTH: 20
<212> TYPE: DNA
<213> ORGANISM: Corynebacterium glutamicum

```
<400> SEQUENCE: 15
ggtgagttgc atacgtggtt                                            20

<210> SEQ ID NO 16
<211> LENGTH: 20
<212> TYPE: DNA
<213> ORGANISM: Corynebacterium glutamicum

<400> SEQUENCE: 16
ttacgccgcc gagaatctga                                            20

<210> SEQ ID NO 17
<211> LENGTH: 20
<212> TYPE: DNA
<213> ORGANISM: Corynebacterium glutamicum

<400> SEQUENCE: 17
agtactaatt gcggtggcag                                            20

<210> SEQ ID NO 18
<211> LENGTH: 20
<212> TYPE: DNA
<213> ORGANISM: Corynebacterium glutamicum

<400> SEQUENCE: 18
cgtcatcgtt gtcgacagtg                                            20

<210> SEQ ID NO 19
<211> LENGTH: 20
<212> TYPE: DNA
<213> ORGANISM: Corynebacterium glutamicum

<400> SEQUENCE: 19
cgccattgct gagcattgag                                            20

<210> SEQ ID NO 20
<211> LENGTH: 20
<212> TYPE: DNA
<213> ORGANISM: Corynebacterium glutamicum

<400> SEQUENCE: 20
cggttgttgc gcttgaggta                                            20
```